(12) United States Patent
Cherif-Cheikh et al.

(10) Patent No.: US 11,878,157 B2
(45) Date of Patent: Jan. 23, 2024

(54) SYRINGE-CONNECTOR DEVICE FOR THE SEPARATE ADMINISTRATION OF CONTROLLED QUANTITIES AT LEAST TWO PRODUCTS IN A SINGLE INJECTION

(71) Applicant: EDIX SA, Lxembourg (LU)

(72) Inventors: Roland Cherif-Cheikh, Castelldefels-Barcelona (ES); Tabatha Bourgois, Barcelona (ES); Lluis Pareta Beltran, Castellbisball-Barcelona (ES); Frederic Lacombe, Sant Cugat Del Valles (ES); Laurence Lachamp, Gava Barcelona (ES)

(73) Assignee: EDIX SA, Luxembourg (LU)

( * ) Notice: Subject to any disclaimer, the term of this patent is extended or adjusted under 35 U.S.C. 154(b) by 554 days.

(21) Appl. No.: 16/333,800

(22) PCT Filed: Sep. 13, 2017

(86) PCT No.: PCT/EP2017/073045
§ 371 (c)(1),
(2) Date: Mar. 15, 2019

(87) PCT Pub. No.: WO2018/050709
PCT Pub. Date: Mar. 22, 2018

(65) Prior Publication Data
US 2019/0255260 A1  Aug. 22, 2019

(30) Foreign Application Priority Data
Sep. 15, 2016 (FR) ........................................ 1658632

(51) Int. Cl.
*A61M 5/32* (2006.01)
*A61M 5/19* (2006.01)
(Continued)

(52) U.S. Cl.
CPC ........... *A61M 5/3294* (2013.01); *A61K 38/09* (2013.01); *A61K 38/24* (2013.01); *A61K 38/26* (2013.01);
(Continued)

(58) Field of Classification Search
CPC .............. A61M 5/3294; A61M 5/2066; A61M 5/2448; A61M 5/284; A61M 5/31596;
(Continued)

(56) References Cited

U.S. PATENT DOCUMENTS 3,680,558 A    8/1972  Kapelowitz
3,896,805 A  * 7/1975  Weingarten ........... A61M 5/284
                                                              604/191
(Continued)

FOREIGN PATENT DOCUMENTS

EP     0 909 155 A1   4/1999
WO       9746202 A1  12/1997
(Continued)

OTHER PUBLICATIONS

International Search Report, dated Dec. 4, 2017, from corresponding PCT/EP2017/073045 application.
(Continued)

*Primary Examiner* — Tasnim Mehjabin Ahmed
(74) *Attorney, Agent, or Firm* — NIXON & VANDERHYE

(57) ABSTRACT

The invention relates to a syringe-connector device comprising, in particular, a hollow plunger including an open inner channel, which plunger can move inside a reservoir, said reservoir being open at one end in a distal connection, for the separate administration of controlled quantities of at least two products in a single injection.

20 Claims, 10 Drawing Sheets a)

b)

(51) Int. Cl.

| | |
|---|---|
| A61K 38/09 | (2006.01) |
| A61K 38/24 | (2006.01) |
| A61K 38/26 | (2006.01) |
| A61K 38/28 | (2006.01) |
| A61M 5/315 | (2006.01) |
| A61M 5/34 | (2006.01) |
| A61M 5/46 | (2006.01) |
| A61M 5/50 | (2006.01) |
| A61M 5/178 | (2006.01) |
| A61M 5/31 | (2006.01) |

(52) U.S. Cl.
CPC .............. *A61K 38/28* (2013.01); *A61M 5/19* (2013.01); *A61M 5/31511* (2013.01); *A61M 5/31513* (2013.01); *A61M 5/31596* (2013.01); *A61M 5/345* (2013.01); *A61M 5/46* (2013.01); *A61M 5/50* (2013.01); *A61M 2005/1787* (2013.01); *A61M 2005/3128* (2013.01); *A61M 2005/31598* (2013.01)

(58) Field of Classification Search
CPC ........ A61M 5/19; A61M 5/345; A61M 3/005; A61M 2005/1787; A61K 38/09; A61K 38/24; A61K 38/26; A61K 38/28
See application file for complete search history.

(56) References Cited

U.S. PATENT DOCUMENTS

| | | | |
|---|---|---|---|
| 3,911,916 A | 10/1975 | Stevens | |
| 3,923,058 A | 12/1975 | Weingarten | |
| 4,014,330 A * | 3/1977 | Genese | A61M 5/2429 604/88 |
| 4,439,184 A | 3/1984 | Wheeler | |
| 4,609,371 A | 9/1986 | Pizzino | |
| 4,702,737 A | 10/1987 | Pizzino | |
| 4,723,937 A | 2/1988 | Sarnoff et al. | |
| 5,080,649 A | 1/1992 | Vetter | |
| 5,599,312 A * | 2/1997 | Higashikawa | A61M 5/3129 604/191 |
| 6,349,850 B1 * | 2/2002 | Cheikh | A61M 5/002 222/1 |
| 6,902,543 B1 | 6/2005 | Cherif-Cheikh et al. | |
| 2002/0058035 A1 * | 5/2002 | Garnick | A61P 5/06 424/145.1 |
| 2008/0208137 A1 * | 8/2008 | Fago | A61M 5/31596 604/191 |
| 2010/0286513 A1 * | 11/2010 | Pollard, Jr. | A61M 5/31511 600/432 |
| 2011/0092906 A1 | 4/2011 | Bottger et al. | |
| 2013/0018311 A1 * | 1/2013 | Denning | A61M 5/2448 604/110 |
| 2013/0144262 A1 * | 6/2013 | Kuhn | A61J 1/1406 604/506 |
| 2013/0267932 A1 | 10/2013 | Franke et al. | |
| 2014/0103045 A1 | 4/2014 | Bottger | |
| 2014/0276039 A1 | 9/2014 | Cowan et al. | |
| 2018/0264195 A1 * | 9/2018 | Hopkins | A61M 5/32 |

FOREIGN PATENT DOCUMENTS

| | | |
|---|---|---|
| WO | 0126718 A1 | 4/2001 |
| WO | 2012/072559 A1 | 6/2012 |
| WO | 2014/124993 A1 | 8/2014 |

OTHER PUBLICATIONS

FR Search Report, dated May 15, 2017, from corresponding FR 1 658 632 application.

* cited by examiner a)

b)

a)

b)

a)

b)

c)

a)

b)

a)

b)

a)
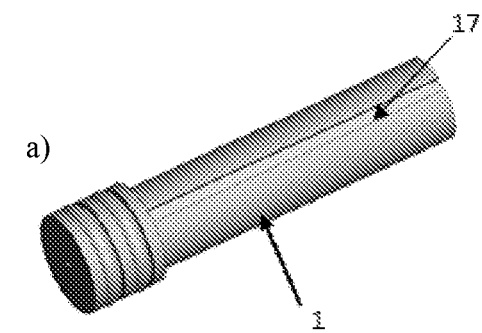
b)
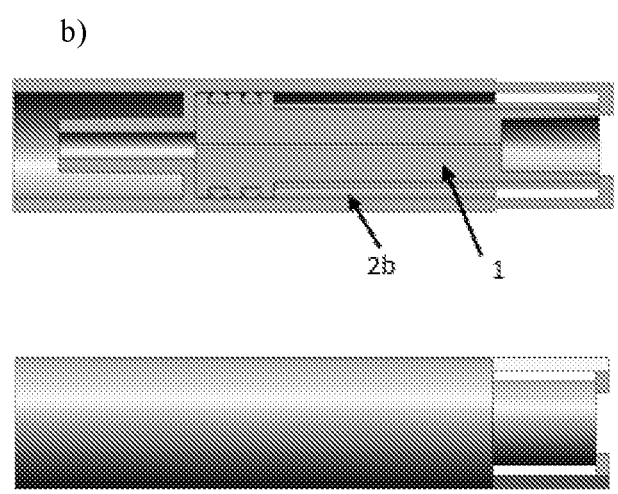
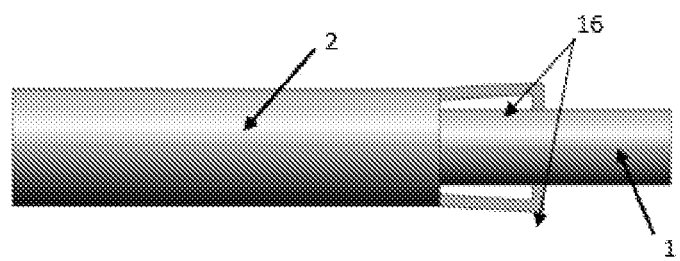
Figures 9a) and 9b)

SYRINGE-CONNECTOR DEVICE FOR THE SEPARATE ADMINISTRATION OF CONTROLLED QUANTITIES AT LEAST TWO PRODUCTS IN A SINGLE INJECTION

BACKGROUND OF THE INVENTION

Field of the Invention

The present invention relates to a device of the "syringe-connector type".

By this expression, the applicant company intends, in the present application, to define a device comprising a "connector-type" part with at least two proximal or upstream and distal or downstream connections, connections that can be connected to injection devices and devices comprising a "syringe type" part which comprises one or more plungers which can be actuated as those of the injection devices for example manually by the user.

This "syringe-connector type" device makes it possible to separately administer at least two products in variable quantities by a single needle left in place without changing the injection device. It is more and more common to have to administer to a patient different injectable forms at the same time.

It is then desirable to limit as much as possible the number of injections to be made by the medical staff and the number of punctures to be received by the patient. However, it is sometimes useful, preferable or even essential to separate the injected products which does not allow to mix them and thus combine these injectable forms in a single injection.

This can lead to situations in which one must perform one after another, several injections on the same part of the body of the patient. It may be difficult to find healthy, regenerated or non-traumatic areas of skin to practice multiple injections, especially in the case of chronic treatments where these needs for injections are frequently renewed every day and over an extended period of time.

Among the many possible uses of the devices according to the invention, mention may be made of the various injectable solutions used in the chronic treatment of diabetes such as fast acting, intermediate acting, slow acting or basal insulins, their premixed forms and analogues of GLP-1 (Glucagon-Like Peptide 1) or other peptides or active molecules. These treatments can be offered in injectable multidoses in the form of flasks, taken and injected with insulin-type syringes or in the form of an injector pen, injected with double-pointed screw needles.

The treatments can also be in the form of an injection for each treatment, some repeated several times a day, with the result of reaching a high number of daily injections. It is known that it is very important to alternate injection sites to keep the skin healthy. It is also known that the rapidity of adsorption of these injectables subcutaneously, may vary according to the injection areas in the body, the fastest, abdomen then arms, to the slowest, thighs and buttocks. To control and reproduce the therapeutic responses, it is therefore also desirable to inject each treatment each time in the same body area. This explains the need to find solutions to combine these treatments into a reduced number of injections.

One of the difficulties is that these treatments are often very personalized and evolving during the patient's life, and that it is then necessary to adapt the doses of each treatment to each patient and to each injection time.

More generally, it is known that injectable drugs are not the drugs best accepted by the patients, who are afraid of injections for fear of needles and pain, or by the medical staff, who know the risks of infection and the need for asepsis of the treatments that are more complicated and longer with injections than with oral medications.

It also leads to higher costs that make all innovations that can simplify injectable treatments economically justified and interesting.

Despite these constraints, the number of injectables is increasing, partly because the new biotechnological treatments use as active ingredients large fragile molecules that are not compatible with the oral route, and because the newly treated pathologies, for example in endocrinology or oncology, involve more complex treatments, with products that have to be combined, as well as more accuracy constraints for the doses, speed of action of the drug and problems of bioavailability. Many efforts are made to try to reduce these constraints related to injectables which all tend towards the same objective: to offer the best treatment to the patients by limiting as much as possible the disadvantages of the injections, and therefore logically, especially for the chronic treatments and/or for multi-therapy, seeking, in the future, also to administer the treatments with the least possible number of injections.

This approach is not only an approach for the comfort for the patient, making savings or for health security, it is more and more often essential. For example, because the repetition and/or the burden of the injectable treatments is accompanied by a local tolerance problem, to the point where it sometimes becomes difficult for the patient's body to regenerate or heal the injured sites to allow acceptable injections on the surface of its skin.

Injection tolerance is particularly critical in children and infants, especially intramuscularly. Although this route of administration is to be avoided in pediatrics, IM is sometimes the only possible recourse for treatment.

This is in particular the case of vitamin therapy for infants with chronic cholestasis, who receive an injection of fat-soluble vitamins every month. This injection is painful for the child, and problematic for the parents, who must continue at home the treatments initiated at the hospital.

One of the solutions found by the health care personnel to overcome this pain during the injection is to precede it by administering a dose of local anesthetic to the same injection site, then proceed to the injection of the therapeutic dose. The local anesthetic may be for example lidocaine, procaine, bupivacaine, ropivacaine, articaine or trimecaine.

This solution can be adapted for all injectable treatments, whatever the injection zone (intradermal, subcutaneous, intramuscular . . . ). Some injectable drugs known to those skilled in the art to be painful at the injection are, for example antibiotics, heparin, certain vaccines (Tetanus) or other products, such as for example promethazine (Phenergan®), corticosteroids and glucocorticoids such as methylprednisolone, antianemic drugs, vitamins, among others; these drugs could benefit from this injection technique to reduce pain during the administration.

To avoid stinging twice in the same area, practitioners recommend injecting the vitamin with the same needle left in place 1-2 minutes later. The injection technique, which consists in disabling the syringe of the needle left in place, makes it possible to administer two vitamins with a single cutaneous breakthrough by modifying the orientation of the needle in order to change the muscular plane.

This injection technique allowing to inject two products through the same needle has many inconveniences, as for example related to the tight disassembly of the connection luer or luer-lock needle-syringe, involving strength and can hardly be done without performing undesired movements that can cause pain.

In addition, it is not advisable to leave an open needle planted in the tissues, which can create an entry point for possible infections. Indeed, in hospitals the risk of nosocomial infections is as high as 5% of the patients, 1 in 20 patients hospitalized, and increases to 25% when linked to invasive procedures, the germs being transported by medical devices.

This technique, while allowing the injection of two products into a single needle bite, is not optimal and may be inconvenient for both the health care personnel and the patient, in addition to increasing the possibility of creating an infectious site at the injection site.

Current solutions to reduce the number of injections, which consist in combining these treatments in the same formulation or in the same injection device, provide only partial answers to these needs. These solutions fix, for example, intermediate ratios between each combined treatment and they can only associate a very limited number of products, according to approaches that correspond to averages rather than to the specific treatment of each patient in each situation.

Reducing the number of injections also meets other needs, for example in the case of injections of therapeutic agents for veterinary use where it is often difficult to have the animal accept several consecutive injections or with livestock for human consumption for which it is crucial to limit the areas of administration and traces or residues of injections. The standards in this sense are very restrictive and it is sometimes difficult to find the right solution to treat these animals while maintaining the healthiest tissues possible without affecting the quality of the production.

The simplest solution to reduce the number of injections would be to mix the different products to be injected, but in practice the question often arises of their compatibilities. It is very difficult to predict the possible interactions for all possible combinations of the many injectables. This mixing approach is therefore often risky, it presents problems of therapeutic efficacy or even of tolerance of the treatments so combined. If reducing the number of punctures for the patient and thus of the sites affected for the same treatment is a useful progress in the face of multi-injection treatments, in many cases this can often not be achieved by the simple solution of the mixture of two products in multiple proportions, and even less so with more than two products, without in-depth knowledge of the consequences of each of these mixtures.

DESCRIPTION OF THE RELATED ART

To limit the number of injections, there are already some approaches to combine at least two products in a single injection, however these devices only provide a solution to some of the problems raised and which are summarized here:
  for the patient: limitation of pain, improvement of the comfort of treatment, limitation of the number of sites of injections especially in chronic treatment,
  for the medical staff: simplicity and speed of the administration procedure, safety, maintenance of the asepsis, response to the risks related to the incompatibility of the mixture of the different products,
  for the manufacturer and distributors: simplicity, speed of registration, adaptation to the needs of variation of treatments, competitiveness with other competing solutions,
  for registration authorities: health security, lower cost for certain treatments, speed of care, treatment by less qualified staff, self-medication.

To the knowledge of the applicant, the solutions to these problems in the prior art can be summarized as follows:

The first existing approaches are those of a combination of two products in the same formulation (hereinafter referred to as "combo-formulations").

These "combo-formulations" options consist in finalizing and developing as new products very specific combinations where two therapeutic agents are formulated together in the same composition. The physicochemical incompatibilities between therapeutic agents, the stability problems, the constraints of volumes that can be administered in relation to the separated products or the needs of new and complete clinical studies greatly limit the progress of these combined treatments. The costs also create limitations on the industrial development of such approaches.

An example of such a fixed ratio combo-formulation is the product Xultophy® from the company NOVO NORDISK, which is a combination of long acting insulin or basal insulin already commercially available only in the Tresiba® product and a GLP-1 analogue already marketed alone in the Victoza® product. This combo-formulation cannot cover all the combined needs of these two products, this does not apply either to patients already treated with two injections or to the needs of combinations between basal insulin and GLP-1 analogues in which it is desirable to propose to the patient a personalized or progressive ratio or treatment between his long-acting or basal insulin and his GLP-1 or analogous peptide.

Similarly, the company SANOFI is developing a comparable product (Lixilan®) for combo-formulation in the form of two products combining basal insulin Lantus® and the analogue of GLP-1 Lyxumia®. Another example of a combo-composition is described in application WO2014/124993. As for the previous examples, one of the limitations is that it is necessarily a fixed ratio mixture whereas each patient needs a gradual treatment according to different specificities for the combination of treatments put in place.

The other approaches considered are those of a combination of two products in the same device.

These device options are geared towards medical technology solutions to meet the same needs to combine different injectables into one product and to perform fewer injections, without resorting to new pharmaceutical compositions but using physical barriers through administration devices.

The objective remains the injection of several products with a single needle implantation, without mixing the fluids or liquids to be injected and/or reducing as much as possible their contact to obtain effects comparable to those of their separate injections. Here too, it is most often, in practice, the combination of only two products.

There are generally two main approaches to this problem: either the products are placed in two reservoirs in Y or in parallel, or they are placed in reservoirs in line or one behind the other.

The first solution is for example to place two products in parallel next to each other, usually in two separate reservoirs that open into the same Y connection. The reservoirs can be operated by the same system or by two systems having separate pressure or transfer systems. These devices are bulky, more voluminous than conventional injection devices. They allow the products to remain separate, but they do not eliminate the risk of cross contamination or possible chemical incompatibilities.

Similarly, it is complicated in these cases not to inject the two products in a fixed dose/volume ratio.

At the time of administration, it remains difficult to prevent the two products from mixing in the connection to the single needle, all along the common injection channels, according to an agitated or dynamic process, which increases the risks of compatibility problems between the two products and limits the applications according to the types of products and their compatibilities in injectable liquid forms.

A single needle injection device for liquids arranged in a "parallel" reservoir arrangement is disclosed in U.S. Pat. No. 4,609,371, this system has the major disadvantage of being wider than conventional injection devices.

In order to seek to meet the limits posed by the operation in parallel of the two plungers the application WO2012/072559 proposes a device in which these movements are controlled by independent motors controlled by an electronic device, for dosing at will the injected volumes of each product. This leads to a complex assembly, expensive and dependent on conventional or rechargeable batteries.

An example of application of such a device combines the delayed-release or basal Glargine insulin otherwise marketed alone in the Lantus® product and a peptide analogue of GLP-1 already marketed alone in the product Lyxumia®. In this case too, it is a fixed ratio of injection between the two products.

The second solution consists in placing the two products in a line, one behind the other. These devices are less bulky or voluminous than the systems in parallel, but the products are less easily, or less effectively separated or isolated in the storage process phase and in the injection phase. They are therefore subject to greater risk of cross-contamination. They must often be filled in less conventional reservoirs, according to more specific, less validated, less universal and therefore more expensive methods.

It is complicated, or even impossible in these cases not to inject the two products in a fixed dose or volume ratio. This does not allow to adjust their doses as needed.

In U.S. Pat. No. 3,911,916 a device is described in which a double-pointed needle pierces the plungers at the end of the injection and thus makes it possible to sequentially put the compartments (or chambers) placed downstream in contact with the injection needle. We can also mention U.S. Pat. No. 3,923,058 which describes a similar device.

More recently devices have been developed around bi-compartmental syringes with in most cases a by-pass made in the cylinder. These packages are expensive and complex and may pose specific sealing or stability problems. Examples of such presentations include the devices described in U.S. Pat. No. 5,080,649, US2011092906 or US2014103045.

Other approaches have been proposed to the by-pass problem starting from a single reservoir segmented by plungers as in the case of U.S. Pat. No. 4,439,184.

In U.S. Pat. No. 4,723,937 the device comprises a single reservoir and an intermediate plunger: the distal (or downstream) part is emptied by this plunger which is positioned in a part which acts as a bypass by deforming the plunger in order to empty the proximal (or upstream) part.

In U.S. Pat. Nos. 3,680,558, and 4,702,737 the device uses a system with two or more reservoirs that flow into each other. This solution involves different and specific reservoirs, becoming thinner from the downstream to the upstream, so necessarily having a smaller volume, which may require to lengthen the whole device until quickly ending up with a length incompatible with the usual distance of the gesture injection. These specific devices include fixed doses and pre-filled presentations.

In applications WO 0126718 and WO 9746202 there is described a device in which a proximal or upstream injection reservoir, such as a cartridge, can be used as a rod on an independent plunger which carries a connection system to this upstream reservoir in order to collapse and therefore empty the contents of a distal or downstream injection reservoir, such as a syringe, during the injection of the contents thereof through a needle. This approach has been repeated in application US2014/0276039.

In the application US 2013/0267932 the upstream reservoir may be a cartridge, in this particular case actuated by an injector pen. This solution presents risks of cross-contamination, with the possibility that the first downstream product comes into contact with the second upstream product in the multi-dose cartridge. Another disadvantage is that this first downstream product injected remains of unique dose type, pre-filled at fixed dose.

In the patent application US 2010/0286513 there are also cited other devices that provide solutions to deliver different injectables by a single puncture, either with 2 syringes in parallel or in line with telescopic reservoirs. In U.S. Pat. No. 3,680,558 there is described a "telescoping compartments" having a valve opening and closing under the effect of the rotation of the plunger, refillable, but this device is complex and imprecise.

BRIEF SUMMARY OF THE INVENTION

The syringe-connector device according to the invention offers a new answer to all these needs. It allows to combine all these treatments at all doses or ratios depending on the specific case of each patient at each moment of the evolution of his disease.

The applicant has invented devices of a new "syringe-connector type" as defined above which provide new solutions and general application to all existing needs to limit injections in all treatments that require multiple injectables.

As indicated above, even if there are some solutions to meet these needs, they generally allow to combine only two specific products in pre-filled systems and/or specific application. They do not open the field of possible applications and combinations and are only punctual solutions to an unresolved much more general problem.

Definitions

The following definitions will be used throughout the present application:

By reservoir it is meant a volume contained in the device that may contain a product, preferably cylindrical in shape.

By seal it is meant a compressible flexible element capable of making hermetic contact between 2 rigid parts, preferably a circular butyl rubber ring.

By luer or luer-lock nozzle it is meant the standard male or female end of frustoconical in shape syringe on which is fixed by contact the standard female end of the needle.

By injector pen adapter it is meant a specific and removable plastic part which transforms the injection needle of the device according to the invention into the equivalent of the internal needle of an injector pen needle. This piece serves as a decoy to screw the injector pen on one of the ends of the device according to the invention, as well as protection to hide the injection needle until the time of administration.

By universal/standard solution are defined the products that can be administered and are contained in standard containers and known to those skilled in the art such as vials, bags, ampoules, cartridges, bottles, syringes and injector pens. It is not necessary to modify them in order to be able to administer them with the reservoir device according to the invention By plunger it is meant the movable part inside the body of the device or reservoir separating two products. It allows emptying by sequentially collapsing the content of the chamber of the reservoir which is downstream.

By hollow it is meant a part pierced by a connection channel permanently open without the need for a closing-opening mechanism, allowing the passage of products from the proximal portion to the distal portion.

By sequential administration it is meant, administrations performed one after the other but continuously, without there being any contact between the products during the process.

By distal it is meant the area of the device closest to the administration zone. It can also be defined as the downstream part of the device taking as reference the movement of the fluid through a device.

By proximal it is meant the area of the device furthest from the injection zone. It can also be defined as the upstream part of the device taking as reference the movement of the fluid through a device.

By product it is meant without limitation and by way of example, substances, agents or therapeutic or prophylactic preparations in the form of injectable formulations, liquid, solid or semi-solid or fluid, pasty or gels. Preferably, the products are liquids or fluids in general.

By injection it is meant the passage of products one after the other by the same channel to end in the same area. This terminology can therefore also be applied to other situations such as, for example, the administration of therapeutic or prophylactic agents by means of a needle, topical or ophthalmic administrations or in all other fields of application.

By unrestricted connections and by way of example are meant standard connections or universal male or female connectors, luer, luer-lock, screw, septum, needle.

The following descriptions are only a few advantageous examples of embodiments of the device according to the invention, which may be implemented according to other specificities also covered by the invention.

The devices and methods of the present invention utilize in-line arrangements, but unlike some of the foregoing solutions, the syringe-connector devices according to the invention may be non-pre-filled, they adapt to all doses/volumes, to all combinations of injection devices of all standard injectable presentations and they are used according to existing methods of extemporaneous preparations.

As noted above, on-line solutions that use the approach of an upstream reservoir entering the downstream reservoir condition and limit the shapes and volumes of each of the injection reservoirs and increase the length of the assembly. This also limits the accuracy of the dosages that are performed by these reservoirs as compared to the devices according to the present invention in which the diameters of the inner hollow plunger are independent of the reservoir volumes of the connected injection devices and dosages, and their accuracy are ensured by these independent reservoirs which reduces the length of the device, similar to that of a standard injection system.

The present invention which includes an internal plunger always open is also a much simpler solution than, for example, the valve or septum systems and is independent of the characteristics of the products to be combined for filling as for injection.

Surprisingly, the Applicant has now discovered the way to avoid complex solutions, expensive and long to develop to obtain with devices consisting of a small number of basic parts, advantages of simplicity and ease of use, while allowing all possible combinations with standard preparatory tools and procedures for the filling-preparation, control, priming and injection.

BRIEF DESCRIPTION OF THE FIGURES

FIG. 1 shows a syringe-connector device in an embodiment comprising on the hollow plunger, a female luer (or luer-lock) connection (1a) and on the reservoir, a male luer-lock connection (2a).

FIG. 2 shows a syringe-connector device in an embodiment comprising, on the hollow plunger, a female luer (or luer-lock) connection (1a) and on the reservoir, a fixed needle (4).

FIG. 3 shows the syringe-connector device in an embodiment similar to that of FIG. 2 wherein is added to the fixed needle of the reservoir, a separate connection injector pen adapter (11).

FIG. 4 shows the syringe connector device in an embodiment comprising a solid plunger (12) and a hollow plunger (1).

FIG. 5 shows details of the reservoir and the solid plunger in its position after use of the syringe connector device.

FIG. 6 shows a syringe connector device according to the version of FIG. 4 with a injector pen adapter in a method of association with two injector pens.

FIG. 7 shows a syringe connector device according to the version of FIG. 2 with a luer stopper (8) on its proximal connection, in its method of association with a vial of injectable product (9).

FIG. 8 shows a syringe-connector device according to the version of FIG. 2 with a stopper on the needle of its distal connection, in its method of association with two syringes of injectables.

FIG. 9 shows the syringe-connector device in a version with a locking mechanism after use and needle depth.

DETAILED DESCRIPTION OF THE PREFERRED EMBODIMENTS

Figure 1:
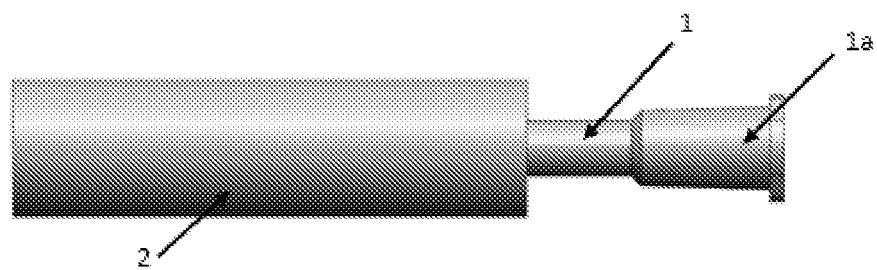
FIGS. 1 to 9.
Figure 1:
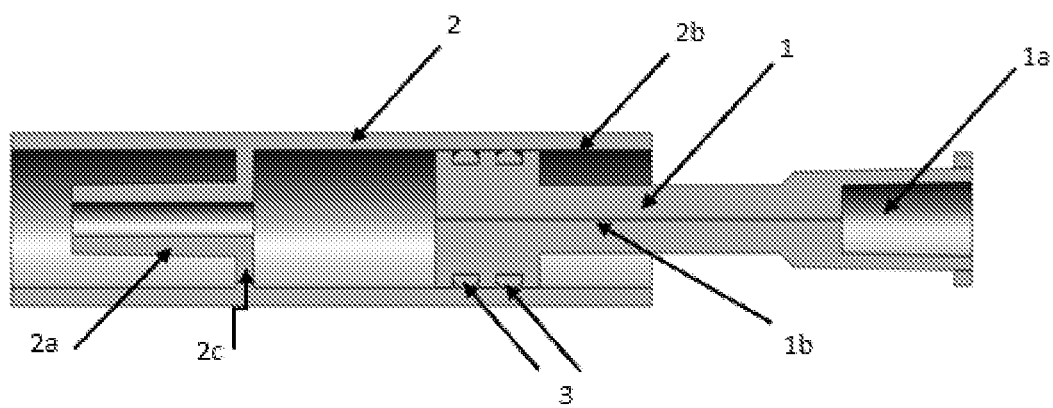

A first object of the present invention is a syringe-connector type device for separately administering at least two products in controlled quantities through a single injection, comprising a hollow plunger (1) that can be moved within a reservoir (2) characterized in that:

said hollow plunger (1) is open by an internal channel (1b), from the end inserted inside said reservoir (2) to the other end in a proximal connection (1a) said hollow plunger (1) forms a sealed barrier with the inner wall (2b) of said reservoir (2) and in its stroke varies the volume or volumes of said reservoir (2) according to its position from one end to the other to the interior of said reservoir (2) and;

said proximal connection (1a) remains constantly accessible outside said reservoir (2) and Said reservoir is open at one end in a distal connection (2a) and at the other end so as to introduce and allow said hollow plunger (1) to circulate.

The devices according to the invention can be for single use at a very interesting cost as compared to the improvements of treatments that they allow. These devices operate manually according to the same principles as current connector and syringe devices, and require no assistance, motor, conventional batteries or rechargeable batteries.

The products are preferentially administered sequentially, in the desired order, at controlled rates and times and with possible site variations or administration depths from the same initial injection point.

The syringe-connector type devices according to the invention may be made in different sizes and with different types of proximal and distal connections. They offer a universal solution for all combined administrations or injectable co-treatments that are problematic, regardless of the products to be administered and their specific constraints or the field of use. They can be adapted to all the products to be administered, such as, for example, all liquid injectables in the form of solutions or suspensions, previously lyophilized or not.

As indicated above, the invention proposes a device for the single injection of at least two liquid products, solid or semi-solid, which at the same time makes it possible to avoid any contact between the products, can make it possible to inject a wide range of volumes capable of adapting to all treatments, can use all current injection devices such as needles, syringes, injector pens, cartridges or infusion systems bottles or other pockets and can be simple, economical to manufacture and have a reduced dimension compatible with these devices.

In particular, the device according to the invention for the injection of at least two products such as for example two therapeutic fluids, into the tissues of a patient, comprises at least one hollow plunger which delimits at least one interior chamber with a variable volume adapted to contain at least a first product in a reservoir;

said hollow plunger in said reservoir is always open by an internal channel in the form of an inner conduit connecting its downstream end to its upstream end in a proximal connection, said conduit opening in this way to the outside of the device;

said reservoir is also open at its downstream end in a distal connection which can carry an injection element such as a needle;

said hollow plunger is slidably movable in said reservoir in a sealed manner and is sufficiently long so that its upstream end in the form of a proximal connection which can carry an injection device such as a syringe, remains accessible outside the reservoir body itself when the plunger collapses the bottom of the reservoir downstream.

The upstream end of said hollow plunger is capable of being actuated and/or grasped by the user to move it in translation.

Said hollow plunger can act as a plunger rod and alone collapse the reservoir, without said injection device having to enter said reservoir.

Said hollow plunger makes it possible to connect the outlet of said reservoir which can carry a needle, to another source of product in another downstream injection device and independent of said device.

The proximal connection of said hollow plunger may be one of the adapters that allow its direct connection to conventional injection systems such as for example and without limitations, luer, luer-lock, screw, septum or needle.

This device is compatible with all sizes of syringes and all types of injection reservoirs and with possible use not pre-filled by extemporaneous filling of two or more products.

The passage of the products, preferably liquid, in the still open channel of the hollow plunger can be done in both directions. The filling of the reservoir can be done by both ends which allows all types of arrangements and loads.

In a particular version of the syringe-connector device according to the invention, a solid plunger is added to the reservoir. This solid plunger is independent of the hollow plunger, it will isolate the downstream volumes from the upstream volumes of the reservoir and put them in communication with the distal outlet of the reservoir by a modification of the surface of said reservoir when said full plunger is at the bottom of said reservoir.

The present invention more particularly relates to a device as described above and comprising at least one, preferably a single solid plunger (12) movable within said reservoir (2) characterized in that:

the at least said solid plunger (12) is introduced into said reservoir (2) before the introduction of said hollow plunger (1) and said inner wall (2*b*) has from said bottom (2*c*) of said reservoir (2), preferably over a distance substantially equal to the thickness of said solid plunger, a variation of its section intended to break the sealing between said solid plunger (12); and said inner wall (2*b*) of said reservoir (2), preferably an increase in its diameter (18*a*)

With the exception of the distance on which said inner wall (2*b*) has a variation of its section (18*a*), said solid plunger (12) forms a sealed barrier with said inner wall (2*b*) of said reservoir (2)

When said solid plunger (12) is in contact with said bottom (2*c*) of said reservoir (2) it is no longer sealed with said inner wall (2*b*) of said reservoir (2); which allows said products to pass between said solid plunger (12) and said inner wall (2*b*) of said reservoir (2).

The present invention more particularly relates to a device as described above and comprising a single solid plunger (12).

In one embodiment of the invention, to allow the passage of the volume of the product or products located upstream of the solid plunger (12) one can achieve a surface variation of the at least one solid plunger, for example in the form of at least one slot or groove.

The subject of the present invention is therefore a device comprising at least one solid plunger (12), preferably a single solid plunger, characterized in that the at least one solid plunger comprises on its distal face a surface variation, preferably at least one slot or one groove (18*b*).

In one embodiment of the invention, the inner wall (2*b*) has from said bottom (2*c*) of said reservoir (2), preferably over a distance substantially equal to or slightly greater than the thickness of said solid plunger a variation of its section intended to break the sealing between said solid plunger (12) and said inner wall (2*b*) of said reservoir (2), preferably an increase in the diameter of the section (18*a*).

When the variation of the section of the reservoir consists of an increase in the diameter of said section, the expression increasing diameter (18*a*) means that in practice the diameter of the inner wall of said reservoir may have an increase over a certain length. This increase in diameter may be greater from 1% to 50% relative to the diameter of the solid plunger.

The limited length on which this increase of diameter (of the inner wall of the reservoir) is carried out is also of the same rank of values/percentage with respect to the thickness of said reservoir, and on the remainder of the length of said reservoir the diameter of the plunger and that of the inner wall of said reservoir are substantially identical because the solid plunger forms a sealed barrier with said inner wall.

The length of the portion of the reservoir with a surface increase may be 5% to 60% greater than the thickness of the solid plunger.

Preferably, the diameter of said reservoir may be increased from 1.5% to 30% relative to the diameter of the plunger over a length that may be greater than 10% to 50% with respect to the thickness of the plunger.

Even more preferably, the diameter of said reservoir may be increased from 1.75% to 20% with respect to the diameter of the plunger over a length which may be greater than 15% to 40% with respect to the thickness of the plunger.

Preferably, the diameter of said reservoir may be increased from 2% to 10% with respect to the diameter of the plunger over a length which may be 20% to 30% greater than the thickness of the plunger.

As an illustrative and non-limiting example of the present invention, the inventors have built a prototype according to the invention which was used to inject two liquid products. In this prototype, the diameter of the solid plunger is 8.2 mm and its thickness is 2.75 mm.

In the device produced according to the invention, the diameter of said reservoir was increased by 2.44% with respect to the diameter of the plunger, which leads to a reservoir diameter of D=8.4 mm over a length of 27.27% greater than the plunger thickness which leads to a length of L=3.5 mm.

The expression substantially equal to or slightly greater than the diameter of the plunger also means that preferably, the space between the inner wall and the plunger at the level of the diameter increase is always equal to at least 0.2 mm. In other words, at this level of the reservoir, the diameter of its inner wall must be at least 0.2 mm greater than the diameter of the plunger. The expression substantially equal to or slightly greater than the thickness of the plunger also means that preferably the increase in diameter of the reservoir is always carried out over a distance equal to the thickness of the plunger increased by at least 0.5 mm.

In a preferred embodiment, this increase in diameter over a distance substantially equal to the thickness of the solid plunger is such that when the solid plunger is in this position, a space is thus created between the reservoir wall and the circumference of the solid plunger, space which may be equivalent to the inner surface of the needles or the internal channel, so as not to change at this level the forces required to move the loaded fluids.

Thus, the device according to the invention comprises at least one, preferably a single solid plunger (12) able to move inside said reservoir (2), characterized in that:
- the at least said solid plunger (12) is introduced into said reservoir (2) before the introduction of said hollow plunger (1) and
- said inner wall (2b) has from said bottom (2c) of said reservoir (2), preferably over a distance substantially equal to the thickness of said solid plunger, a surface or diameter increase (18a)
- With the exception of the distance on which said inner wall (2b) has a surface or diameter variation (18a), said solid plunger (12) forms a sealed barrier with said inner wall (2b) of said reservoir (2)
- When said solid plunger (12) is in contact with said bottom (2c) of said reservoir (2) it is no longer sealed with said inner wall (2b) of said reservoir (2); which allows the passage of said products between said solid plunger (12) and said inner wall (2b) of said reservoir (2).

The present invention may for example combine the approach described above which seeks to combine an existing product pre-filled injector pen but with the advantage of combining it with other existing pre-filled products such as a another injector pen while varying the doses of each product as desired to adjust to each patient according to its specific treatment, particularly in accordance with the current directions of personalized medicine.

The present invention more particularly relates to a device as described above, characterized in that said syringe connector can be connected to one or more administration devices of the syringe type, injector pen, injection bag, bottle, injector, pump, needle, catheter or connector.

Thus, the user can according to his needs connect to the device according to the invention for example syringes and or injector pens and/or infusion systems in their commercial configuration without any need for manipulation or additional development.

He can sequentially discharge the therapeutic or prophylactic agents in the device of the invention without manipulation and proceed to their joint injection according to standard methods.

The device according to the invention may not be a loaded device whose reservoir or reservoirs should, together or separately, be registered as separate specific products.

As it may be a non pre-filled system, it does not necessarily have to solve the potential problems of stability, compatibility and sealing during their lifecycle which certain previously mentioned devices have.

By using the device according to the invention, the patient can receive at least two therapeutic agents in a single injection at different volumes, whatever the presentation in which the injectable therapeutic agents are.

The syringe-connector devices according to the invention are preferably arranged in line so that they can be used as connectors with other injection devices at each of their ends, such as a needle connected to the distal end or downstream and a syringe connected to the other proximal or upstream end and so that they can then be used as syringes at the time of injection.

The present invention more particularly relates to a device as described above, characterized in that the diameter of said internal channel (1b) is the smallest possible that is compatible with the passage of said product to be administered and preferably said diameter is of a diameter greater than or equal to the diameter of the needle duct (4) when the distal connection (2a) is provided with said needle. For example, in order to inject two liquid products (with volumes, for example, between 5 μL and 2 mL), the device may be equipped with a needle that can range from 25 gauge (i.e. 0.5 mm external diameter and 0.3 mm internal diameter) and a plunger pierced with an internal channel of minimum diameter equal to 0.3 mm, preferably 0.4 mm in diameter. For two liquid products, use will preferably be made of a needle of reduced diameter, for example gauge 29 (0.34 mm outside diameter and 0.18 mm internal diameter) and a plunger pierced with an internal channel of minimum diameter equal to 0.18 mm. For the injection of viscous products, the device may be equipped for example with a needle equal to or less than 23 G (i.e. 0.64 mm outer diameter and 0.34 mm internal diameter) with a plunger pierced with an internal channel of diameter equal to or greater than 0.34 mm, or even a 18 G needle (i.e. 1.2 mm outer diameter and 0.8 mm internal diameter) with a plunger pierced with an internal channel of diameter equal to or greater than 0, 8 mm.

In what follows, we mean by connections without limitation and as examples, the standard connections or universal male or female tips, luer, luer-lock, screw, septum, needle. Non-limiting injection devices are, by way of example, needles, catheters, connectors, syringes, injector pens, infusion systems for vials, bags or pumps. The term "product" without limitation and by way of example means substances, agents or therapeutic preparations in the form of injectable, liquid, solid or semi-solid or fluid, pasty or gel formulations.

The connections of the devices according to the invention are preferably standard such as luer, luer-lock or screw-needle so as to make universal adapters on injection devices such as syringes, injector pens or infusion devices.

The present invention more particularly relates to a device as described above, characterized in that said syringe-connector has at its proximal and/or distal ends connections (1a) and (2a) which can be male or female, and be chosen from the luer, luer-lock, screw, needle, septum, valve or device types characterized in that an adapter (11) which allows the fixing of an injector pen to said syringe connector is fixed on said distal connection (2a) around its needle (4).

The syringe-connector devices according to the invention can make it possible to perform this single injection in the various conventional approaches to injections such as, for example, for intradermal, subcutaneous, intramuscular or intravenous injections. This combined injection can be performed exactly at the same site, for example at the exit of the fixed point of injection into any of these tissues. These combined injections can also be performed at different points. According to the arrangement chosen according to the forces of implantation of the needle and collapse of said device, it will be possible, for example, to begin the subcutaneous injection of the most downstream product as soon as the needle is introduced under the skin and continue this injection until it is complete before reaching the deepest point of penetration of the needle where it will be possible to practice in another zone the injection of another product. This separation can also be achieved at fixed points with an arrangement as described below. It is also possible according to the sequential mode of these injections to leave a controlled lapse of time between each injection if it favors the effectiveness of the treatments.

The syringe-connector devices according to the invention allow precise dosages for each of the products or components of the combined injection which depend only on the injection devices to which these syringe connectors are connected and which are therefore equivalent to those obtained in the usual use of these injection devices. These syringe-connector devices therefore also allow adjustable and variable doses for each of the components injected together.

The syringe connector devices according to the invention are preferentially for single use, they are adaptable to all the needs of injectable therapies. They are preferentially filled extemporaneously just before their use but they can also be pre-filled with one or all of the products they must inject.

The devices according to the invention are suitable for the various injectable dosage forms such as liquid, semi-solid or solid forms, for example freeze-dried or in powders, for example the microparticulate delayed-release forms. For example, it may be possible to have only one pre-filled injected product in freeze-dried solid form and to connect the device to the liquid reservoir which contains only its reconstitution mixture.

The syringe-connector devices according to the invention can according to their size and their application, adapt to all the injection volumes, for example since a few tens of microliters for certain applications such as diabetes or veterinary on small animals, up to a few hundred milliliters, or a few liters for example for infusions or for certain veterinary applications on large animals.

The syringe-connector devices according to the invention make it possible to inject a single product. They allow to combine in a single injection the administration of at least two products or even three products maintained separately. They also make it possible to inject more than three products in a single injection.

Each of the injection volumes defined by the syringe-connector devices according to the invention may contain zero, one or more products to be injected or an excipient which will constitute a product to be injected with the contents of another volume which may for example be in solid form. These devices and their volumes may also contain any other substance that would need to be separated until the time and the point where it is desired to bring them together. By injection it is also meant products that pass one after another by the same channel to end up in the same area, this terminology can also be applied to other situations such as for example in the administration of therapeutic or prophylactic agents, topical or ophthalmic administrations or in any other field of application.

The devices according to the invention can be associated with conventional protection systems such as, for example, needle shields.

The present invention more particularly relates to a device as described above characterized in that said syringe-connector is sterilized before filling and is made of materials compatible with the injections, in that said reservoir is transparent and in that said hollow plunger or said reservoir can be graduated.

The present invention also more particularly relates to a device as described above, characterized in that a portion of the distal connection provided with a needle is extended over a diameter comparable to that of said device, up to the cannula of said single needle to provide a support on the skin or the administration area at the time of injection.

The present invention also more particularly relates to a device as described above characterized in that said syringe-connector has a locking mechanism which avoids its reuse and which can control different depths of injection of said single needle when said plunger hollow is introduced to said bottom of said reservoir.

The device according to the invention can be equipped with a safety system or mechanism, which, once the injection is finished covers the needle (shield needle), or with a retractable needle system to reduce the risk of injury by the user (safer device) and ensure its unique use (impossible to reuse the device once the system is activated).

The syringe-connector devices according to the invention may be provided in all sizes compatible with each of their possible applications and for example in the injectable therapeutic area allow variable volumes in each of the chambers created by these devices which may vary from a few microliters, a few milliliters, a few hundred milliliters or even a few liters.

Without being limited to the areas, arrangements and possible sizes of embodiments of these devices, some examples of these sizes and applications will emerge from reading the examples that follow.

The therapeutic applications that can benefit from the device of our invention are numerous. Research efforts today and advances in oncology more and more offer a so-called personalized medicine where each patient often receives a pharmaceutical treatment including several injectable therapeutic agents and doses and frequency that are specific to him.

One of the fields of direct and immediate application of our invention is certainly the field of insulin therapy and the treatment of diabetes in general in which each injectable can be chosen and adapted according to the patient and his diet with possibilities for change to each injection up to several times a day.

By way of illustrative but non-limiting examples of the therapeutic or prophylactic applications of syringe-connector devices according to the invention, mention may be made of diabetes, hormonal therapy, antibiotic therapy, oncology, immunology, vaccines and emergency treatments. This applies to the human but also to veterinarian medicine where the injections are often complicated for example in antibiotic therapy or in other cases of preventive treatments where one can use several injectables.

The subject of the present invention is also the use of a device of the syringe-connector type defined above, characterized in that the products to be administered are used in the treatment of diabetes, infertility, hormonal therapy and oncology as vaccines, or in all treatments in which several close injections must be performed.

The devices according to the invention make it possible, for example, to combine in a single injection and at all the desired doses the Glargine basal insulin marketed in the Lantus®, Basaglar® Toujeo® formulations with the analog peptide of GLP-1 lixisenatide marketed in the formulation Lyxumia® whatever their presentations or injection devices, in injector pens or bottles.

The devices according to the invention allow the injection of different products without contact or mixture between these products before injection. This provides a solution to compatibility problems and allows for example to inject into a single injection products at physiological pH, or close to pH 7, with a product at acidic pH that may precipitate or change at neutral pH, so normally incompatible with these other products and to get the therapeutic responses of all these products as if they had been injected separately.

What is often important is that the injectable touches the body tissues at the injection site in its defined formulation to obtain its mechanism of operation and this does not necessarily or solely depend on the physiological pH encountered. If the mixture before injection is impossible for example because it causes an evolution of each product before injection, injecting the products one after another at the same site without mixing before their formulations does not present the same problems and can be a direct answer to this problem. We can also optimize this by respecting a waiting time between each product as it is already the case with many injectables. It is also possible with the device according to the invention and as will be described in the figures, to deliver in a single injection, one or more products at different depths in distinct tissue areas. Each of these solutions can also be a response to the pain sometimes caused by some of these products such as acid injectables.

Each type of insulin has complementary actions and some patients must inject themselves mealtime insulin before each food intake, i.e. at least three injections per day. The devices according to the invention will make it possible, for example, to combine the injection of Lispro Humalog® first with that of Glargine Lantus®, Basaglar or Toujeo® or Detemir Deglutec®. Premixed insulin or premix such as NovoLog® can also be added or, for example, combine Lantus® with Victoza® or any other GLP-1 or analogue peptides.

An advantage of the devices according to the invention for example in the case of diabetes treatments is therefore to reduce the number of daily injections regardless of the type of insulin, which gives more time to each injection point to recover from the previous injection before proceeding to a new injection at the same site. Even in cases where the basal insulin injection has to be repeated twice a day, this is no longer a problem if these two injections go away because they can be combined with other injections. The fact of being able to combine, for example, each treatment of basal insulin with other injectables, GLP-1, prandial or premixed insulin is more suited to these multiple treatments than the new products in the form of formulations or devices in fixed combinations.

These new combined treatments open the door to the applications of the devices according to the invention according to the same logic, especially to patients who already use these products at all the other different doses of combos-formulations and who are anxious to reduce their number of injection.

The devices according to the invention also apply to children and adolescents where reducing the number of injection is clearly likely to improve compliance.

The present invention also more particularly relates to the use in which several injections are performed using a syringe-connector type device defined above characterized in that at least two products selected from at least one of the following groups a) to (c) are administered in the treatment of diabetes:

(a) insulin or an insulin derivative preferably selected from fast, semi-slow, slow, basal insulin or insulin mixtures such as Tresiba®, Lantus®, Toujeo®, Humalog®, Umulin®, Levemir®, Basaglar®, Actrapid®, NovoMix®, Mixtard®, Apidra®, NovoRapid®, b) GLP-1 or the analogue peptides GLP-1 preferably chosen from Liraglutide (contained for example in the commercial product Victoza®), Lixisenatide (contained for example in the commercial product Lyxumia®), Albiglutide (contained for example in the commercial product Tanzeum®), Exenatide (contained in commercial products Byetta® or Bydureon®), Dulaglutide (contained for example in the commercial product Trulicity®), Semaglutide or Taspoglutide, c) Glucagon or a similar Glucagon, in stable form in solution or in solid form or lyophilized to reconstitute.

In a preferred embodiment of the invention, the present invention also more particularly relates to the use of a syringe-connector type device defined above characterized in that at least two products are chosen in at least two of the groups a) to c) previously indicated.

In a preferred embodiment of the invention, the present invention also more particularly relates to the use in which several injections are performed using a syringe-connector type device defined above, characterized in that two products are administered and that one of the two products administered is insulin or an insulin derivative selected from group a) described above and the other product is GLP-1 or peptide analogues of GLP-1 selected from group b) described above.

In a preferred embodiment of the invention, the present invention also more particularly relates to the use in which several injections are performed using a syringe-connector type device defined above, characterized in that two products are administered and that one of the two products administered is insulin or an insulin derivative selected from group a) described above and the other product is insulin or a derivative insulin selected from the same group a) described above.

In a preferred embodiment of the invention, the present invention also more particularly relates to the use in which several injections are performed using a syringe-connector type device defined above, characterized in that two products. are administered and that one of the two products administered is insulin or an insulin derivative selected from group a) described above and the other product is Glucagon or a Glucagon analogue selected from group c) described above.

In a preferred embodiment of the invention, the present invention also more particularly relates to the use in which several injections are performed using a syringe-connector type device defined above, characterized in three products are administered and in that one of the three products administered is insulin or an insulin derivative selected from group a) described above, the other product is GLP-1 or peptide analogues of GLP-1 selected from group b) described above and the third product is Glucagon or a Glucagon analogue selected from group c) described above.

In a preferred embodiment of the invention, the present invention also more particularly relates to the use in which several injections are performed using a syringe-connector type device defined above, characterized in that two products are administered and that one of the two products administered is GLP-1 or peptide analogues of GLP-1 selected from group b) described above and the second product is Glucagon or a Glucagon analogue selected from group c) described above.

The present invention also more particularly relates to the use as described above in which several close injections are performed using a syringe-connector type device defined above, characterized in that said products to be administered are used in the treatment of diabetes and consist on the one hand of insulin or of an insulin derivative chosen preferably from fast, semi-slow, slow or basal insulins such as Tresiba® products or Lantus® and GLP-1 or peptide analogues of GLP-1, such as liraglutide (contained in the commercial product Victoza®), Lixisenatide (contained in the commercial product Lyxumia®), Exenatide (contained in Byetta® or Bydureon® commercial products) or Taspogluctide; or glucagon or a similar glucagon, in combination with one of the peptides mentioned above, more particularly an analogue of GLP-1.

Said glucagon or glucagon analogue may also be used in emergency treatments related to diabetes, such as hypoglycemia, and because of its instability in solution, be packaged in the device according to the invention in solid or freeze-dried form, and be reconstituted directly in the reservoir just before administration.

The present invention also more particularly relates to the use in which several injections are performed using a syringe-connector type device defined above characterized in that at least two products selected from at least one of the following groups a) to c) are administered in the treatment of female infertility:

a) The GnRH (gonadotropin-releasing hormone) agonists, preferably selected from commercial products Decapeptyl®, Suprefact® or Synarel® b) GnRH (Gonadotropin-releasing hormone) antagonists, preferably selected from commercial products Cetrotide® or Orgalutran® c) follicle-stimulating hormone, preferably selected from the commercial products Gonal-F®, Puregon®, Menopur®, Pergoveris®, Fostimon®.

In a preferred embodiment of the invention, the present invention also more particularly relates to the use of a syringe-connector type device defined above characterized in that at least two products are chosen in at least two of the groups d) to f) previously indicated.

In a preferred embodiment of the invention, the present invention also more particularly relates to the use in which several injections are performed using a syringe-connector type device defined above, characterized in that two products are administered and that one of the two products administered is the agonist GnRH selected from group d) described above and the other product is follicle stimulating hormone selected from group f) described above.

In a preferred embodiment of the invention, the present invention also more particularly relates to the use in which several injections are performed using a syringe-connector type device defined above, characterized in that two products are administered and that one of the two products administered is the GnRH antagonist selected from group e) described above and the other product is follicle stimulating hormone selected from group f) described above.

The present invention also more particularly relates to the use as described above in which several close injections are performed using a syringe-connector type device defined above, characterized in that said products to administered are used in the treatment of infertility and consist on the one hand GnRH agonists preferably chosen from the products Decapeptyl®, Suprefact® or Synarel®, or antagonist GnRH preferably chosen from Cetrotide® or Orgalutran® products and follicle-stimulating hormone, preferably selected from Gonal-F®, Puregon®, Menopur®, Pergoveris®, Fostimon®.

The present invention also more particularly relates to the use as described above of a syringe-connector type device defined above, characterized in that said products to be administered in said volumes are in solid form, half solid, lyophilized or not and are pre-loaded or loaded at the time of use of said syringe-connector device.

The subject of the present invention is also a process for filling a syringe-connector device defined above, comprising, inside an external reservoir body (2), an internal hollow plunger element (1), closing said body reservoir on one side, process characterized in that the products to be packaged are introduced inside said reservoir (2) on the side of a distal connection (2*a*) or on the side of said hollow plunger (1) before or after said hollow plunger (1) is introduced into said reservoir (2).

The present invention also more precisely relates to a method of filling a syringe-connector device defined above, comprising, inside a reservoir (2) partitioned in its volumes by a solid plunger (12) and by a hollow plunger (1), characterized in that the products to be packaged are introduced inside said reservoir (2) on the side of a distal connection (2*a*) after said solid plunger has been positioned in said reservoir or beside said hollow plunger (1), before or after that said solid plunger (12) or said hollow plunger (1) is introduced into said reservoir (2).

The present invention thus relates to a process for preparing and conditioning said product or products in said syringe connector such as, without limitation and by way of example in the form of powder or freeze-dried.

Another subject of the present invention is a method of use and dispensing by which the said syringe connector is extemporaneously filled with the desired quantity or quantities of products, is connected to one or more injection devices and the said connector is used as a complementary injection device through a single needle.

According to the invention, the syringe-connector device is preferably used as a reservoir which can be separately filled with the desired variable quantities or volumes of one or more products and which, connected to one or more injection devices which can contain quantities or volumes of other products according to variable volume ratios, isolates the different products, avoids their mixtures and allows their injection via a single needle.

The present invention also more specifically relates to a method by which said syringe-connector device is used as a device for connecting injection devices for injecting controlled quantities of the product or products to be administered and as a device for injecting the said product or products via a single needle.

Another object of the present invention is to improve the method of needle implantation and fluid flow. The injection gesture, when performed with the device of the invention, also allows the injection of the product contained in the distal reservoir according to a damped mechanism by a phenomenon of "hydraulic plunger", less painful, which allows improved tolerance related to the injection.

The phenomenon of "hydraulic plunger" comes from the arrangement of the device according to the invention, composed of a cylindrical tube, a plunger and an orifice for discharging a fluid, which presses on said fluid and not on a solid element such as in a standard device. The fluid, due to its lower viscosity, has a greater damping capacity, which makes it possible to reduce the injection forces vis-à-vis a solid element, which by its hardness has a lower absorption coefficient.

In addition, this arrangement also regulates the penetration rate of the needle or cannula. In a conventional syringe type assembly, the force is directly transmitted to the needle; in the case of an injection made with too great a force (for example an inexperienced user), or too brutal, this force has a direct effect on the tissues, causing pain for the patient. Regarding the assembly according to the device of the invention, the needle will enter the tissues at a speed corresponding to the process of penetration-cut-tissue lesions obtained depending on the tip and section of the bevel: if the speed is too high the "hydraulic plunger" effect will dampen and slow down this penetration. On the other hand, if the speed of penetration is too slow or is not constant, the phenomenon will avoid fluctuation or too slow penetration of the needle. The devices according to the invention can be obtained by conventional industrial techniques known to those skilled in the art and for example by machining or thermo-molding of plastic parts for example transparent or any other material compatible with its use.

Moreover, as indicated above, the device according to the invention can be subjected to sterilization processes to ensure the maintenance of asepsis at the time of its use.

The syringe-connector devices according to the invention can be manufactured in large series at reduced costs according to standard processes already known and validated for the numerous connectors and injection devices existing on the market. These are generally injection-molding fabrications from the plastics used in these fields.

The constituent parts of the devices according to this invention can be assembled in the same way as, for example, disposable syringes on the same type of machines, in automatic mode and with the same positioning-placement accuracies.

As in these examples, the plungers can be made in the rubbers, silicones or butyls usually used. Separate plungers can be made from these materials or use seals carried by the plastic parts in the grooves or rings provided for this purpose. It is also possible to use existing standard seal elements such as o-rings. As in these examples also of syringes or as in the case of needles for injector pen, it is possible to associate with these plastic parts metal parts such as needles for injection or piercing septa for example by overmoulding or by gluing in these plastic parts.

These assembled parts can also be packaged according to comparable processes, for example individually in blister. They can also be sterilized with the same methods. It is thus possible to obtain these devices in large quantities at costs compatible with their unique use and realize them in the various sizes and with the different assemblies and connections required depending on the field of their applications. The following developments explain in detail and without limitation the characteristics of the invention. These developments are an illustrative reference to the figures attached. However, they are intended to describe embodiments of the invention which are not limited to said figures.

For example, FIG. 1 schematically shows one of the possible embodiments of the syringe-connector device according to the invention for the administration in a single injection of certain product combinations.

In one embodiment of the invention, the hollow plunger (1) is terminated in the upstream portion outside the reservoir (2), by a female-type proximal connection (1a), luer or luer-lock, and the reservoir (2) is completed in the downstream part by a distal connection (2a) of male type, luer or luer-lock.

In general, the hollow plunger (1) is permanently perforated or open with an internal channel (1b) which communicates the interior of the reservoir (2) downstream by the internal part of the proximal connection (1a) to the outside the device upstream.

As indicated above, the internal channel (1b) may be of diameter, shape and variable section but will preferably be made rectilinear, of the smallest possible diameter compatible with the passage of the products used in the syringe-connector device according to forces and acceptable pressures for its use for example manually, so as to reduce the residual dead volumes in said device after use and to ensure the best separation of the different products in the loading or administration phases.

In all cases and for example on the other versions shown in the other figures, the hollow plunger (1) and the internal channel (1b) can be described as in this FIG. 1.

In FIG. 1b, the hollow plunger (1) is represented on the downstream side inside the reservoir (2) terminated by a plunger head of the two-joint type (3), for example of the o-ring type. In the case of this FIG. 1 and in a more general manner, this functional plunger portion can be made according to all the conventional approaches such as for example with one or more independent seals in the form of cylindrical rings engaged in one or more grooves provided for this purpose in the plunger head or in the form of a butyl plunger holed with one or more lips positioned around the plunger head or directly part of the plunger head by a smooth surface or with one or more contact rings.

By these means or by other suitable means, the hollow plunger (1) ensures sufficient contact and sealing on the inner wall (2b) of the reservoir (2) to separate and move said products without leakage. By these means also or by other suitable means, it is also possible to control the forces of fiction to obtain a desired order in the movement of the different pieces together.

For example, in FIG. 1b, the reservoir (2) is shown open downstream in the distal connection (2a) which communicates the interior of the reservoir (2) with the outside of the device downstream.

In general, the distal connection (2a) may comprise, inside its external part in the extension of the external body of the reservoir (2), a specific pitch not shown here, for rotating a connection of luer-lock type with an associated injection device downstream. This outer portion of this distal connection (2a) may also extend as shown herein, so as to provide a wider contact point with the skin at the time of injection.

The hollow plunger (1) is shown here introduced into the reservoir (2) at a medium distance. The hollow plunger (1) can be moved inside the reservoir (2) while maintaining said sealing with the inner wall (2b), from its upstream end to its downstream end in contact with the bottom (2c) of the reservoir (2). These displacements can be operated by actions in translation, performed on the proximal connection (1a) of the hollow plunger (1). These displacements can also be operated under the influence of the volumes of said products introduced or extracted from said reservoir.

In general, it is possible, for example, to position a standard female luer stopper on the distal connection (2a) and a standard syringe filled with the volume of a first product on the proximal connection (1a) and to move said hollow plunger from the bottom (2c) to an upstream position in said reservoir which will depend on said volume transferred from said standard syringe. For example, it is also possible to position a standard male luer stopper on the proximal connection (1a) and the end of a catheter connected to an injection device on the distal connection (2a) and to move said plunger according to said volumes to be transferred.

Figure 2:
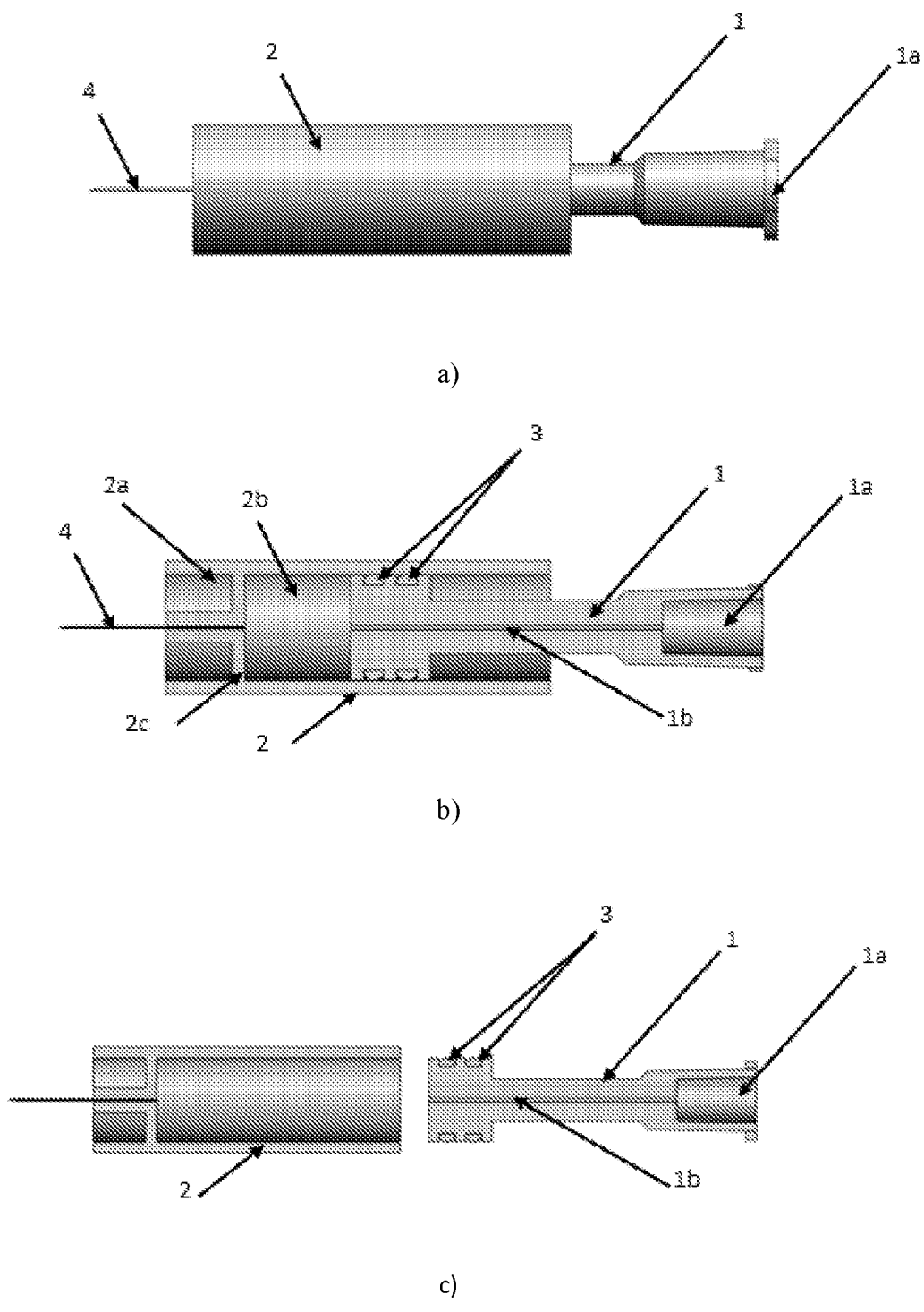

For example, FIG. 2 schematically shows one of the possible embodiments of the syringe-connector device according to the invention for the administration in a single injection of certain product combinations.

In one embodiment of the invention, the hollow plunger (1) is terminated in its upstream portion external to the reservoir (2), by a proximal connection (1a) of the female, luer or luer-lock type, and the reservoir (2) is completed in the downstream portion by a fixed needle type (4) distal connection (2a).

The reservoir (2) is shown open downstream in the distal connection (2a) by a fixed needle (4) which communicates the interior of the reservoir (2) with the outside of the device downstream. This distal connection (2a) may include an outer portion which may extend as shown herein, so as to provide a wider contact point with the skin at the time of injection.

The hollow plunger (1) is represented here either introduced into the reservoir (2) at an average distance (FIG. 2b) or before its introduction, outside the reservoir (2) in front of the upstream opening of the reservoir (2) by which it is introduced (FIG. 2c).

This assembly preferably takes place during the manufacture of said device, before its packaging for example in individual blister. Said hollow plunger (1) can be moved inside the reservoir (2) while maintaining said sealing with the inner wall (2b), from its upstream end to its downstream end in contact with the bottom (2c) of the reservoir (2). These displacements can be operated by actions in translation, performed with the proximal connection (1a) of the hollow plunger (1). These displacements can also be operated under the influence of volume changes of said products inside the reservoir (2).

For example, it is possible to position a standard butyl stopper, not shown here, on the fixed needle (4) of the distal connection (2a) and a standard syringe filled with the volume of a first product A on the proximal connection (1a) and move said hollow plunger from the bottom (2c) to an upstream position in said reservoir which will depend on said volume of said product A transferred from said standard syringe. It is also possible, for example, to position a standard male luer stopper on the proximal connection (1a), to pierce the septum cap of a vial and to take a volume of a first product A by actuating the hollow plunger (1) by the upstream portion of its proximal connection (1a). In both cases, one can then fix for example a pre-filled syringe of the volume of a second product B on the proximal connection (1a) and practice the injection in sequence of the two products A then B, by the same fixed needle (4).

Figure 3:
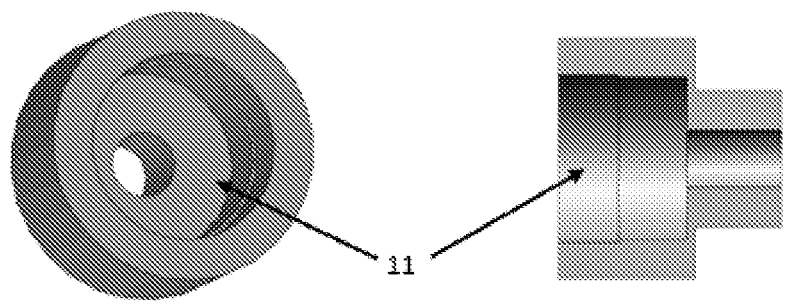
Figure 3:
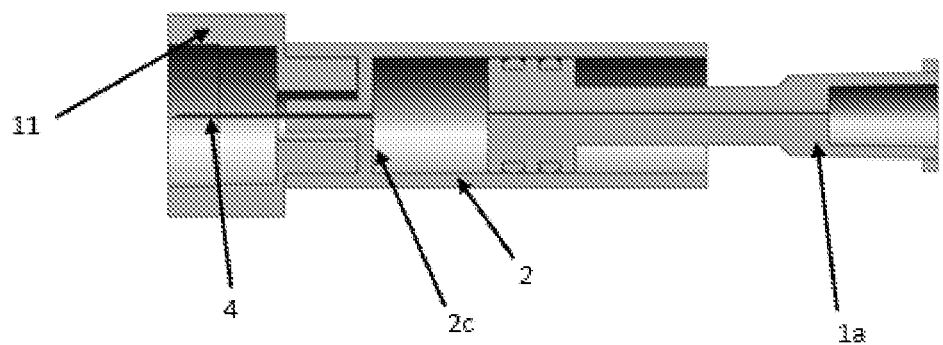

For example, FIG. 3b diagrammatically represents the syringe-connector device in the embodiment of FIG. 2 associated with a complementary piece or connection (FIG. 3a) separate injector pen adapter (11) which forms part of the invention.

In one embodiment of the invention, the injector pen adapter (11) is positioned in the distal connection (2a) at the downstream end of the reservoir (2). Thus positioned, the injector pen adapter (11) reproduces a connection comparable to the standard screw and needle connections of the injector pens in which the needle portion is provided by the fixed needle (4).

A general mode of use of the devices according to the invention can be described as follows:

If a standard male luer stopper or a syringe filled with a product B (not shown in FIG. 3) is previously placed on the upstream end of the hollow plunger (1) at its proximal connection (1a), one then can then screw any injector pen on the downstream end of the reservoir (2) to load a dose of product A, controlled and transferred by said injector pen according to the same steps or operations of its usual use protocol for injecting directly this dose of product A. One can then unscrew said injector pen, remove said injector pen adapter and practice the injection with said syringe filled with a product B fixed on said proximal connection (1a) by implanting the fixed needle (4) at the chosen injection site. For example, the product A is first injected, holding said syringe at its finger support and the base of its plunger rod and pressing the hollow plunger (1) into the reservoir (2) until it touches the bottom (2c) and collapses the reservoir (2). The product B will then be injected from said filled syringe, according to the protocol of its usual use, by action between said finger support and said plunger rod. In this way, product A and then product B will have been injected at a single point of implantation of the fixed needle (4) without contact and without mixing the two products. If necessary, it will be possible to respect a precise time between the injection of the product A and that of the product B by marking a controlled pose between these stages, as it is already practiced for many injections.

Figure 4:
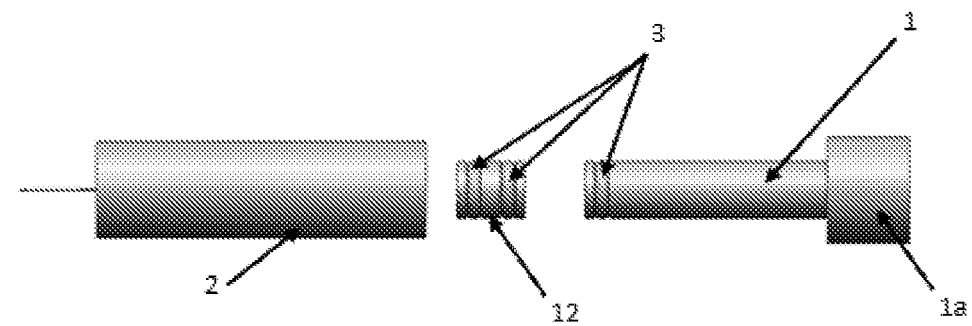
Figure 4:
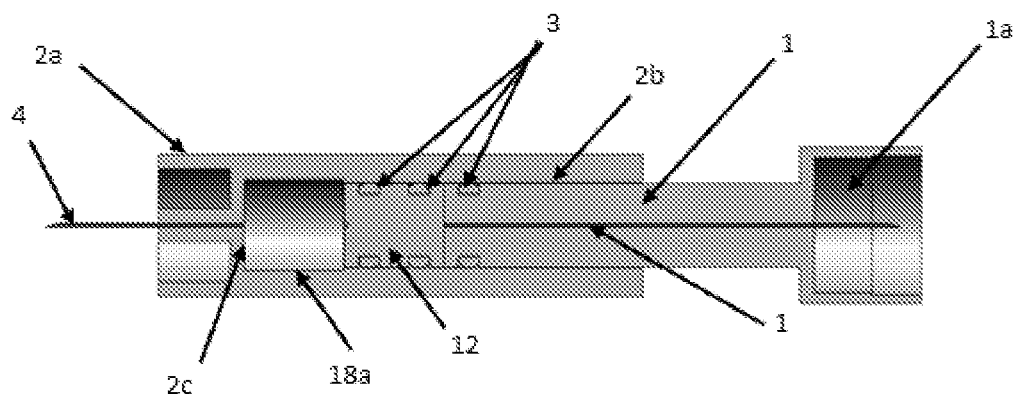
Figure 4:
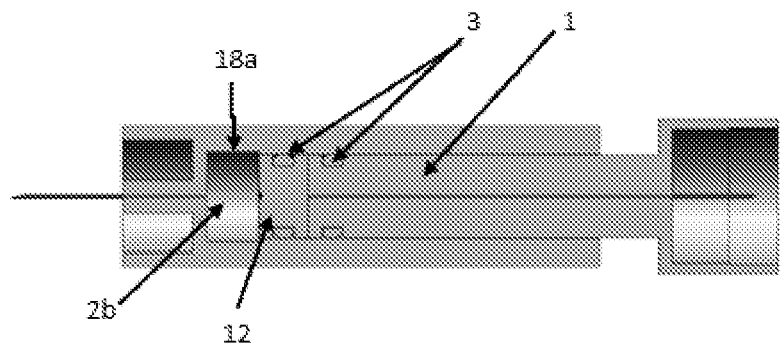

For example, FIG. 4 diagrammatically shows the syringe connector device in an embodiment comprising a solid plunger (12) and a hollow plunger (1) according to one of the possible arrangements of said syringe-connector device according to the invention for enabling the administration of two, three or more products in a single injection without mixing and without contact between products according to certain possible combinations of these products.

In one embodiment of the invention, the hollow plunger (1) is terminated in its upstream portion external to the reservoir (2) by a proximal connection (1a) of the standard screw and needle type such as that of the needles for injector pens and the reservoir (2) is completed in the downstream portion by a distal connection (2a) of fixed needle type (4).

The hollow plunger (1) is permanently perforated or open with an internal channel (1b) which communicates downstream a portion of the interior of the reservoir (2) located between the hollow plunger (1) and the solid plunger (12) with upstream, the inner portion of the proximal connection (1a) outwardly of said device. This internal channel (1b) can for example be described and produced in the same manner and with the same objectives as in FIGS. 1 and 2.

The hollow plunger (1) is shown on the downstream side inside the reservoir (2) terminated by a plunger head of the one seal type (3) for example of the o-ring type. This plunger head portion may for example be described and made in the same manner and with the same objectives as in FIG. 1.

The reservoir (2) is shown open downstream in the distal connection (2a) by a fixed needle (4) which communicates the interior of the reservoir (2) with the outside of the device downstream. This distal connection (2a) may include an outer portion which may extend as shown herein, so as to provide a wider contact point with the skin at the time of injection.

The solid plunger (12) is shown in FIG. 4b and FIG. 4c introduced into the reservoir (2) downstream of the hollow plunger (1) at the precise position it must occupy after assembly or montage of the various parts of said device at the time of manufacture and before use. The hollow plunger (1) is shown in a preferred position before use, in contact with the rear of the solid plunger (12). The solid plunger (12) is in a position which can enable it to go upstream to the inside of the reservoir (2) if necessary, according to the volume or volumes of products loaded into the reservoir (2) by its distal connection (2a) at the time of filling said device and in a displacement that can drive the hollow plunger (1) which touches it upstream. In this configuration no contact is possible between the products and their volumes loaded downstream of the solid plunger (12) and those loaded upstream of the plunger (12). In the reservoir (2) downstream of said precise position of the solid plunger (12) there is a portion in which the inner wall (2b) of the reservoir (2) has a variation in the diameter of the inner wall (18a) which makes that when the solid plunger (12) moves downstream of said precise position, the volumes and products downstream and upstream of the solid plunger (12) can be put into communication in a manner which allows for example their transfers around the solid plunger (12) for their administration through the fixed needle (4).

Figure 5:
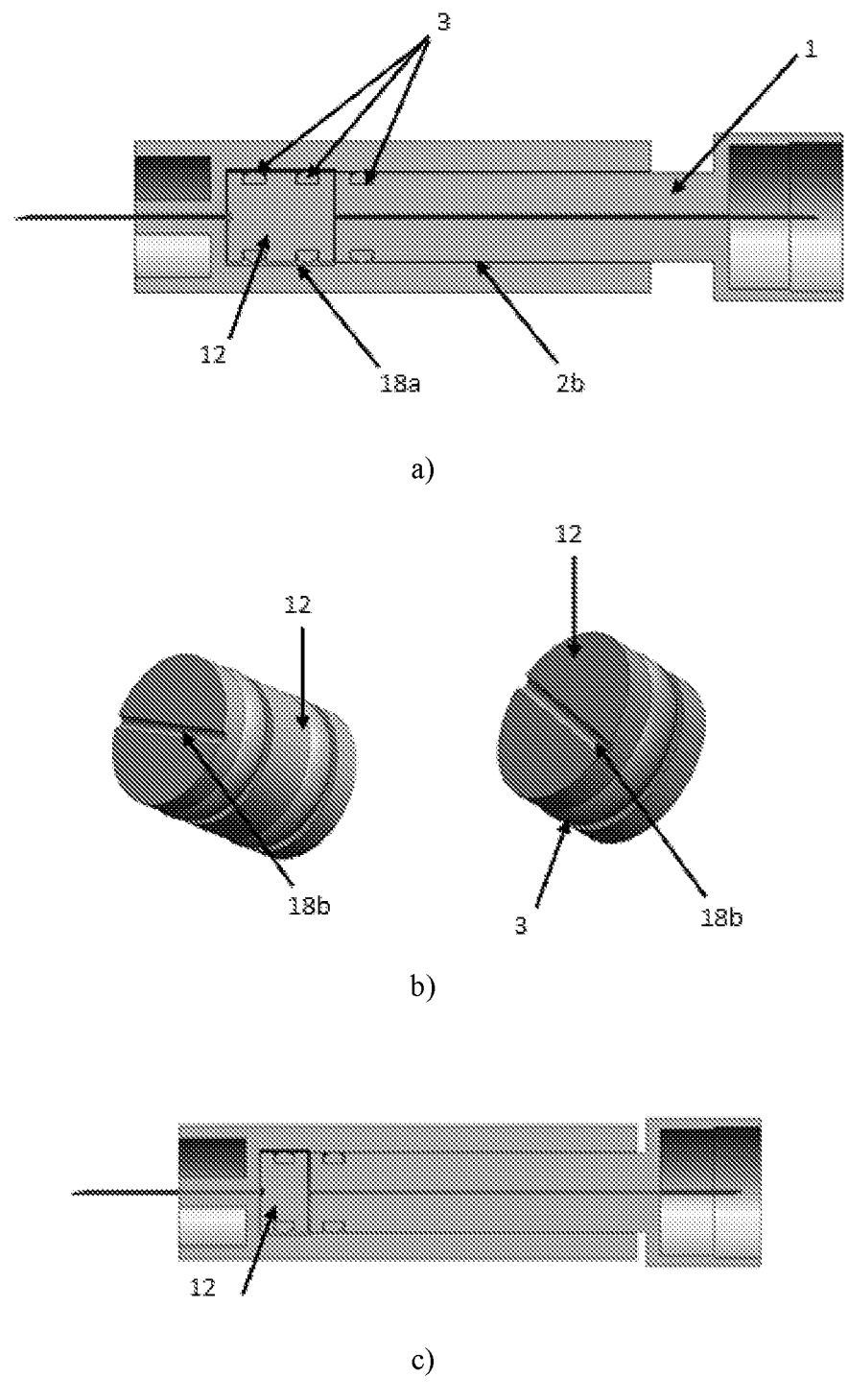

In FIGS. 4b and 4c, the solid plunger (12) is represented at its precise position inside the reservoir (2) in two plunger configurations with separate o-ring type seals, first with two seals. (3) then with a single seal (3) so as to limit the dead volumes of products after use of said device as is further specified with FIG. 5.

This solid plunger (12) can be made according to all conventional approaches such as for example as here, with one or more independent seals in the form of cylindrical rings engaged in one or more grooves provided for this purpose in the plunger head or under shape of a solid butyl plunger with one or more lips around the plunger head such as for example the intermediate plunger of the bi-compartmental syringes with bypass or like a plastic part molded with a smooth surface or with one or more contact rings. By these means or other suitable means, the solid plunger (12) ensures sufficient contact and sealing on the inner wall (2b) of the reservoir (2) to separate and move the volumes of said products. An example of the use of this type of syringe-connector device with solid plunger (12) from two injector pens to inject 2 products in a single puncture will be specified next with FIG. 6.

Another general mode of use of the devices according to the invention can be described as follows:

If it is desired, for example, to inject in a single injection the doses of three different products A, B and C, for example one, A, is totally incompatible with the other two B and C, this type of syringe-connector device can be used with solid plunger (12) in a version in which the proximal connection (1a) of the hollow plunger (1) is of the luer or luer-lock type, so that standard syringes can be attached thereto. In this embodiment, if an injector pen adapter (11) is added to the distal connection (2a), a volume of product A can first be loaded from a standard injector pen screwed onto the injector pen adapter (11) in this distal connection (2a) on the downstream side, it is then possible to connect a first syringe which contains the volume of product B and charge it between the solid plunger (12) and the hollow plunger (1). This first syringe is then disconnected to connect a second syringe loaded with the product C. The injector pen adapter (11) is removed downstream and the product A is firstly injected through the fixed needle (4) by operating the hollow plunger (1) by its proximal end (1a). one can then pause enough for this product A to be effective or diffuse from its injection point then inject the product B by actuating the hollow plunger (1) from the syringe held at the level of its finger support and its plunger rod. If necessary, one can mark a second pause. Product C is then injected by operating the syringe in a standard manner.

In another embodiment of the syringe-connector device with solid plunger in which the distal connection (2a) of the reservoir (2) is also of the luer or luer lock type, the same operation can be carried out and three products contained for example in three flasks from three syringes. The first syringe connected downstream to the distal connection (2a) will then be discharged into said device, for example through another standard female-female connector of the luer or luer lock type. For example, it is possible to disconnect this first downstream syringe only after having filled said device with the contents of the second syringe and having connected upstream the third syringe with its contents. One can then for example fix a standard needle or a standard catheter terminated by a needle on the distal connection (2a) of said device and practice the injection of the three products as before, at a single point without mixing them.

These processes will be the same for the injection of more than three products with the possibility of also having more intermediate plungers allowing the separation of different semi-solid or solid liquid products.

For example, FIG. 5a and FIG. 5c schematically show details of a possible arrangement of the reservoir (2) and the solid plunger (12) in its so-called bypass position during use or after use of the syringe connector device according to the invention.

In one embodiment of the invention, when the solid plunger (12) has finished its sealed movement inside the reservoir (2) from upstream to downstream of the reservoir (2), it can arrive at the contact of the bottom (2c) in a part of the reservoir (2) where it ends its course and where it loses its sealing with the inner wall (2b) of the reservoir (2) through a variation of the section of the inner wall (18a). This section variation of the inner wall (18a) is sufficiently large to allow the volume of the product (s) upstream of the solid plunger (12) to flow downstream of said device with manually usable forces and pressures. This variation of the internal section (18a) is small enough not to constitute a too important dead volume lost for this or these products. This variation of the section of the inner wall (18a) may for example provide an opening of section comparable to that of the internal channel (1b) or transfer or of the injection needles used in each configuration of said device for each type of application.

As indicated above, this variation of the section of the inner wall (18a) is intended to break the sealing between the solid plunger (12) and the inner wall (2b) of the reservoir (2). As also indicated above it may for example be obtained by a slight increase in the internal diameter of the reservoir (2), This rupture of the sealing may also be obtained by a deformation of the circle of the section of the reservoir (2).

The present invention also includes any other variations capable of breaking the sealing between the solid plunger (12) and the inner wall (2b) of the reservoir (2) such that at least one slot or groove along the inner wall (2b) over a given length from the bottom (2c) of the reservoir (2), for example.

For example, FIG. 5b also schematically shows an example of surface variation of the solid plunger (18b). When the solid plunger (12) reaches the bottom (2c) of the reservoir (2), it may be necessary to have a surface variation of the solid plunger (18b) which will prevent the solid plunger (12) from clogging the downstream outlet of the reservoir (2) through the distal connection (2a) and for example in the case shown here of a fixed needle outlet (4).

In one embodiment of the invention, to allow the passage of the volume of the product or products located upstream of the solid plunger (12 a surface variation of the solid plunger (18b) can be achieved in the form of at least one slot or groove.

It will be possible, for example, to ensure that the depth thereof is sufficient so that the entire volume flow of the product or products situated upstream of the solid plunger (12) can flow without this passage leading to a force or a pressure greater than that encountered in the other parts of said device. This surface variation of the solid plunger will also advantageously be the smallest or the finest possible to limit the dead volumes.

For example, FIG. 5b shows two schematic versions of this surface variation of the solid plunger (18b) with a solid plunger (12) with two seals (3) and a second with a seal (3) capable of limiting said dead volumes.

For example, FIG. 4a also schematically shows an exploded view of the various parts of said device before assembly. The solid plunger (12) is shown between the reservoir (2) and the hollow plunger (1), outside of the reservoir (2) in front of the upstream opening of the reservoir (2) through which it is introduced. According to a preferred assembly order, in the manufacture process the solid plunger (12) will first be introduced in the reservoir at the precise position, for example before the bypass zone, which it occupies before use of said device and then the hollow plunger preferentially in contact with the solid plunger (12). This exploded view also makes it possible to better visualize a possible surface variation of the inner wall (18a) of said bypass zone on the inner wall (2b) of the reservoir (2). According to one embodiment of this type, the internal diameter of the reservoir (2) in cylindrical form increases sufficiently so that the solid plunger (12) is no longer sealed with the wall (2b) and that the volumes of the product or products in upstream of the solid plunger (12) can flow downstream according to forces and pressures for example compatible with their manual injection.

Figure 6:
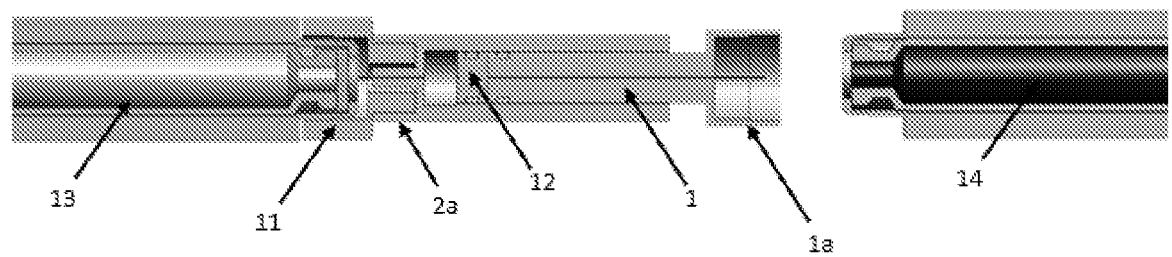
Figure 6:
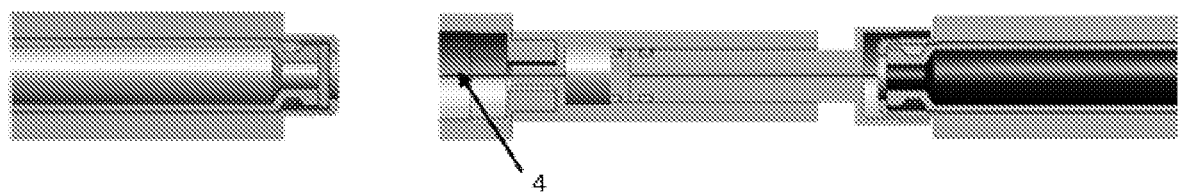

For example, FIG. 6 schematically shows one of the syringe-connector devices of FIG. 4 in a version with a solid plunger (12) and a hollow plunger (1) in the reservoir (2). The hollow plunger (1) is terminated in its upstream part by a proximal connection (1a) of the standard type with screw and needle like that of the needles for injector pens and the reservoir (2) is finished in the downstream part by a distal connection (2a) of fixed needle type (4) in which is positioned an injector pen adapter (11).

In one embodiment of the invention shown in FIG. 6a, an injector pen A (13) containing a product A, for example incompatible with a product B, is screwed onto this injector pen adapter (11) and a volume of the product A previously selected and controlled by said injector pen A (13) is loaded by actuation of said injector pen A (13) in the reservoir (2) downstream of the solid plunger (12). Said volume according to its importance, can move the solid plunger upstream in the reservoir (2). Said pen A (13) is then unscrewed from the injector pen adapter (11) and a second injector pen B (14) containing a product B, as shown in FIG. 6b, with a volume previously selected and controlled by this injector pen B (14) is screwed onto the proximal connection (1a). It is then possible to remove the pen-connector adapter (11) and inject the product A and then the product B according to operations comparable to those described above and close to the standards of use of these injection devices.

During preparation before injection, the injector pen adapter (11) also acted as a needle protector. In this example, the needle (4) of said syringe-connector device can be stitched as it would be for a injector pen needle and then push on the body of said injector pen B (14) to collapse said device and inject said product A. It will then be possible to pause the effectiveness of said product A and then to inject said product B as is usually done with said injector pen B (14). The syringe-connector and injector pen assembly B (14) is then removed from the injection site. The said device is unscrewed from said injector pen B (14) by its proximal connection (1a) and said device is eliminated as a standard injector pen needle, for example by recapping it with the injector pen adapter (11), before unscrewing it. These injector pens A (13) and B (14) can then be stored as normally recommended before their next use without risk of cross-contamination by said products A and B. Said volumes A and B can be adapted to each case or each treatment as in their usual separate use and injected at one time without any contact or risk between these products.

Figure 7:
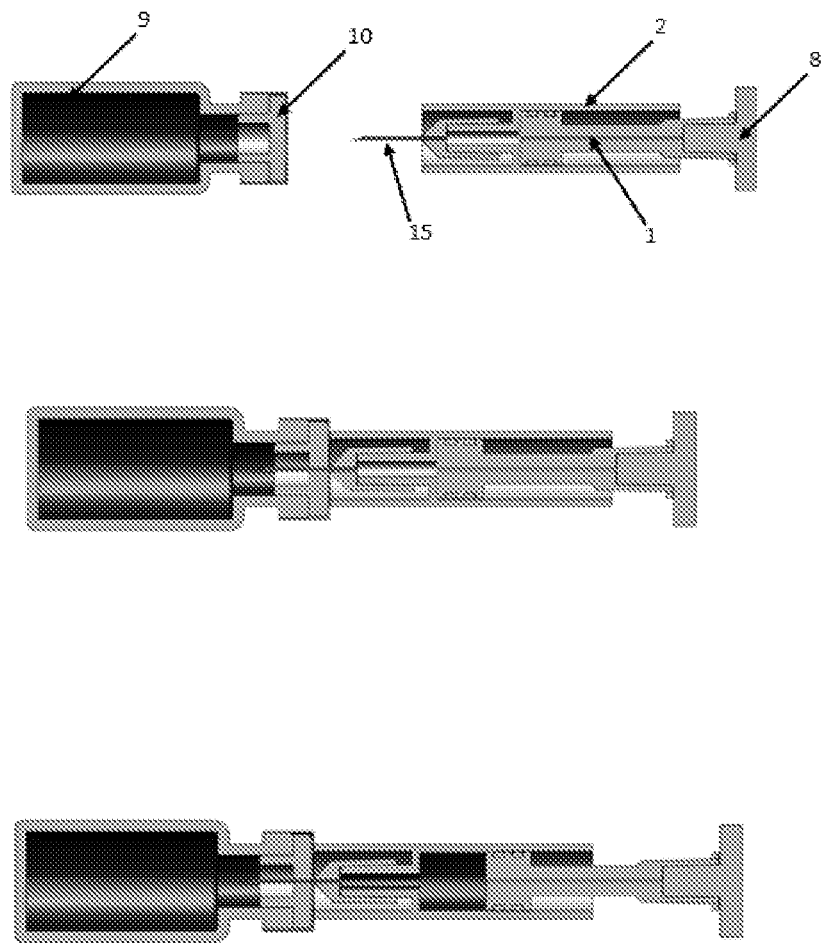

For example, FIG. 7 schematically represents a situation in which a syringe-connector device according to the invention is connected to a standard needle (15) on the luer or luer-lock end of the distal connection (2a).

In one embodiment of the invention, if a standard male luer stopper (8) is attached to the proximal connection (1a), said device can be used to take the volume of a first product A, for example through the septum-stopper (10) inside a multi-dose vial (9) of product A. The reservoir (2) is then loaded with the volume of this first product A to be injected. Then one disconnects said device from the bottle (9), one can keep or change the standard needle (15). If one then removes said standard male luer stopper (8) and if a luer or luer-lock syringe charged with the volume of a second product B to be injected is connected to the luer end of the proximal connection (1a), one can implant the standard needle (15) and first inject the first product A and then the second product B, without mixing the products A and B, at a single point of insertion on the skin of said standard needle (15). The air contained in the internal channel (1b) will keep products A and B separated until they are injected.

One operates in this case with said device as would be done with a standard syringe using the hollow plunger (1) by its proximal end (1a) as if it was a plunger rod and for example here, pricking the needle (15) through the stopper-septum (10) of a vial (9) to take the desired volume of the product A. Preferably in this case the body of the reservoir (2) is transparent and graduated so as to dose said volume of said product A transferred into said device by the translation of the hollow plunger (1). Another solution may be to graduate the hollow plunger (1) on its outer surface with a scale that allows to control said sampled volume even in a non-transparent reservoir. A graduated scale on the outside of the hollow plunger (1) can also be in all the applications of said device, a means of verifying the volume transfer (s) and thus of controlling the operation of said device and of the injection device (s) which are associated with it. In the case shown here, once said device loaded with a volume of product A taken from the vial (9) and the standard needle (15) removed from the septum stopper, it may also be possible to use said device as a syringe and directly inject its content of product A through the standard needle (15).

If, as previously described, said standard male luer stopper (8) is removed to fix in its place, for example, a syringe loaded with another product B, the two products A and B can be injected one after the other according to the steps also described.

In this case, as in all cases in which a first product A is taken from the downstream side, this product A does not fill the internal channel (1b) of the hollow plunger which remains wholly or partly filled with air. If another injection device loaded with a product B is then connected to the proximal connection (1a) of the hollow plunger (1), it is not necessary to purge the residual quantities of air and the injection can be done directly. In this case the products A and B may not be brought into contact and remain separated from the air layer of the internal channel (1b). Even if a multi-dose injection device of the product B is connected upstream on the proximal connection, its contents will not be contaminated by the product A and the injection device may be reused several times as it is usually.

Figure 8:
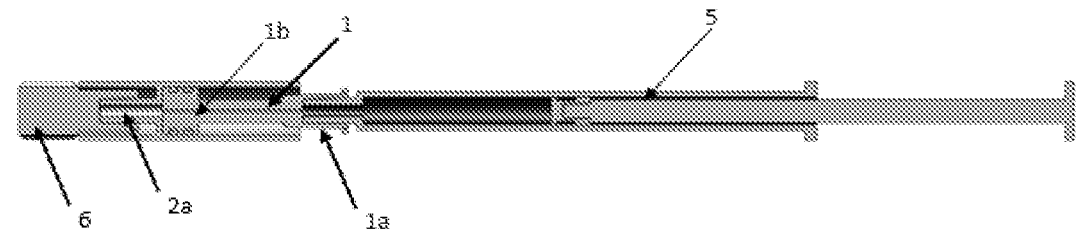
Figure 8:

For example, FIG. 8 schematically shows a use of a version of the syringe connector device in which said device is of the type shown in FIG. 1 with a standard female luer stopper (6) downstream of the reservoir (2) and a connection proximal (1a) luer on which is first attached a syringe of product A (5). In this example the standard luer female cap (6) is positioned to close the distal connection (2a) as is done on syringes pre-filled without needles.

In one embodiment of the invention, once the luer nozzle of a syringe filled with a product A (5) is connected to the proximal connection (1a) one can normally operate this syringe and load a dose of product A controlled by it, as shown in FIG. 8a. The product A passes through the internal channel (1b) and fills the reservoir (2) of said device by moving the hollow plunger (1) upstream. The syringe with product A is then disconnected and a syringe of product B (7), is connected to the same upstream end, as shown in FIG. 8b, the standard luer female cap (6) can then be removed and then fix a standard needle on this distal connection (2a), and perform the injection of A and B at one time according to steps described for the previous figures. This standard needle will not have previously pierced septum before entering the skin. In this case we can have some contact between the products A and B but only within said device and without risk of contact in other reservoirs that may contain these two products if two different syringes are used.

For example, FIG. 9 shows two schematic versions of the syringe-connector device equipped with a locking or locking system which is activated at the end of use or during the injection, which can thus avoid that said device can be reused and who can control the injection depth. Said system can be obtained according to different arrangements or adaptations possible on the only external body reservoir (2), it can also be obtained with arrangements or adaptations on both the reservoir (2) and the hollow plunger (1), it can also be obtained using an additional piece on the reservoir (2).

In another embodiment of the invention, a system of safety valves (16) carried by the reservoir (2) and trough (17) on the outer surface of the hollow plunger (1) in which these safety valves (16) move. At the beginning of the use, the hollow plunger (1) can be in a depressed position in the reservoir (2) but without contact with the bottom (2c), in which position it will arrive only at the end of the use. In this way the hollow plunger (1) can be freely moved upstream during the first phase or phases of use of said device. It can also be freely moved downstream during the following phase or phases of use. In these different phases the safety valves (16) flow freely in both directions in the channels (17). At the end of the use of said device, the hollow plunger (1) reaches the deepest position in the reservoir (2) in contact with the bottom (2c), in which the safety valves (16) emerge from the channels (17) in order to close over the hollow plunger (1) and block all its movements in the reservoir (2) as shown in this FIG. 9b.

Figure 9C:
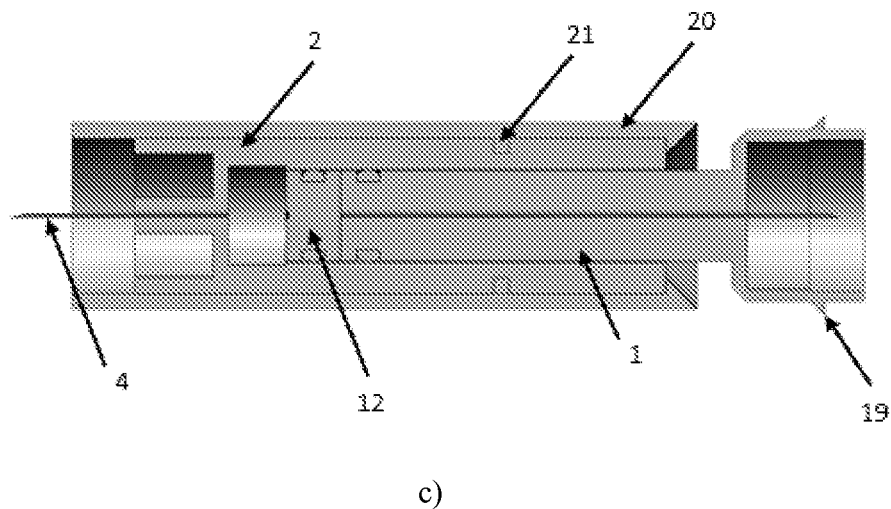

In another embodiment of the invention shown in FIG. 9c, the device comprises a proximal connection (1a) equivalent to the head of a injector pen needle and thus capable of being fixed on all the injector pens. In this embodiment, an additional piece, depth control (19) is added to the reservoir (2). During all the steps of use of said device up to the injection, this depth control part (19) is locked on the upstream part of the reservoir (2). This depth control (19) then only allows to inject a part of the length of the fixed needle (4). After injection of the downstream product or products, when the injection will collapse said reservoir (2) by displacement of the solid plunger (12) in contact with the bottom (2c), said proximal connection (1a) will release said depth control (19) from its locked position on the surface of said reservoir (2) by outing the retaining notches (20) from their compartment and said fixed needle (4) will be able to penetrate deeper tissues at the injection site to administer the upstream product or products. In this way, without any manipulation of said device, one can separate the injection sites of different products administered with said device according to the invention. Said depth control (19) can find a second locking position by means of safety hooks (21) on the surface of said proximal connection which will also serve to lock said device after its use and thus prevent any reuse.

The following examples will illustrate possibilities of using the syringe-connector device according to certain possible modes of operation. The device according to the invention can in particular be declined in different versions and dimensions depending on the characteristics of the products to be injected.

The first (illustrated but not limited for example by FIG. 2) consists of a single hollow plunger (1) pierced with an internal channel (1b) terminated in proximal connection (1a) for example by a female luer tip which is moved relative to the inner wall (2b) of the reservoir (2) to create a chamber between the hollow plunger (1) and the bottom (2c) of the reservoir (2) having a needle (4) for injecting drugs.

This first version can be used, for example, for syringe-vial, syringe-syringe and syringe-injector pen connections. If necessary, a barrier against possible contamination between a product B contained in the connected injection device and the product A contained in the chamber of the syringe-connector device can be ensured by air, in particular in the internal channel (1b) which separates the two products.

The second version (illustrated but not limited for example by FIG. 4) has a solid plunger (12) downstream of the hollow plunger (1) which represents a physical barrier against the possible contamination of the device containing the fluid B by the fluid A contained in the reservoir (2), and which allows in some arrangements the administration of a third fluid C through the same needle (4).

EXPERIMENTAL PART

Example 1 Demonstration of the Functioning and the Precision of Administrations Performed with a Device According to the Invention in a First Configuration Preparation of a Peptide 1 Solution at 200 µg/mL Approximately 50 mg of peptide 1 are weighed and solubilized in 5 ml of 0.1% acetic acid whose weight is also determined by weighing. By a 1/10 dilution from this first solution at 2 mg/ml the final solution at 200 µg/ml is obtained.

Peptide 1 is easily detectable by low concentration HPLC analysis, stable once solubilized in 0.1% acetic acid solution and its properties are known to those skilled in the art.

Slow Human Insulin Solution (Umuline® NPH) at 100 IU/Ml:

This solution is a commercial solution of human insulin marketed by the company ELI LILLY under the name of Umuline® NPH. This product is an intermediate-acting insulin. The solution is contained in a commercial flask of 10 mL at a concentration of 100 IU/mL.

Preparation of the Device According to the Invention for an Insulin Solution at 100 IU/Ml and a Peptide Solution at 200 µg/Ml from a Vial and a Syringe In this configuration, the device is equipped with a standard male luer stopper (not shown in FIG. 2, visible in (8) in FIG. 7), positioned at the end of the proximal connection (1a) of the hollow plunger (1) to transform the hollow plunger into a closed plunger. This conical and standard male piece fits into this luer-lock female end. In this way, it is possible to use the device as a syringe to take a volume equivalent to 5 UI (50 µl) of Umuline® NPH directly from the commercial 10 mL vial.

The wall of the reservoir (2b) being transparent, a first visual check is made to verify that the dose of insulin taken is found entirely in the distal chamber of the reservoir and that the needle (4) of the device is not closed. The wall of the reservoir (2) or the hollow plunger (1) is equipped with a graduation to know the volume of product introduced into the reservoir (2); the device fills up like a needle syringe.

After the distal chamber is filled with Umuline NPH insulin, the syringe containing the peptide volume 1 is prepared from a vial containing the solution. To compensate for the dead volumes of the device, 20 µl, are added to the volume of Peptide 1 to be injected, i.e. a total of 170 µl.

It is not necessary to add a surplus of insulin because once injected, Peptide 1 expels the insulin that could have remained in the distal chamber of the reservoir. The cap that closes the proximal connection (1a) of the hollow plunger (1) is removed to connect the luer tip of the syringe containing Peptide 1. The device is then ready for injection.

Administration of an Insulin Solution at 100 IU/mL and a Solution of Peptide 1 at 200 µg/mL Via the Device According to the Invention:

Firstly, the distal chamber is collapsed, and subsequently the Peptide 1 content in the syringe is injected through the inner channel (1b) using a standard administration procedure. All of the two discharged products are collected in a vial for analysis by HPLC.

Results

The data obtained are grouped in Table 1 (as indicated above, 20 µL, of the solution were added in the syringe to compensate for the dead volumes)

TABLE 1

| | | Insulin discharged (µL) | Peptide 1 discharged (µL) |
|---|---|---|---|
| 20 µL/150 µL (170 µL) | mean | 46.48 | 166.20 |

Example 2: Demonstration of the Operation of the Administrations Carried Out with a Device According to the Invention in a Second Configuration Preparation of Peptide Solution 1 at 200 µg/mL Approximately 50 mg of peptide 1 are weighed and solubilized in 5 ml of 0.1% acetic acid whose weight is also determined by weighing. By a 1/10 dilution from this first solution at 2 mg/ml the final solution at 200 µg/mL is obtained.

Slow Human Insulin Solution (Umuline® NPH) at 100 IU/mL:

This solution is a commercial solution of human insulin marketed by the company ELI LILLY under the name of Umuline® NPH. The solution is contained in a commercial flask of 10 mL at a concentration of 100 IU mL.

Preparation of the Device According to the Invention for an Insulin Solution at 100 IU/Ml and a Peptide Solution 1 to 200 µg/mL from Two Syringes This configuration makes it possible to fill the reservoir via the proximal connection (1a) using two syringes: the first containing 20 IU (20 µL) of Umuline® NPH insulin and the second one containing 120 µl of Peptide 1. The device is equipped with a standard female butyl luer stopper (as shown in (6) of FIG. 8) which covers the needle (4) and prevents the passage of liquids therethrough.

The first Umuline® NPH insulin syringe is filled from a commercial 10 mL vial and is then connected by the male luer cone of the syringe inserted into the female luer tip of the proximal connection (2) of the hollow plunger (1).

Through this connection Umuline® NPH insulin is injected into the distal chamber of the reservoir; the device being obstructed at the other end, the hollow plunger (1) moves as the chamber fills. Once the first syringe is discharged into the device according to the invention, the second syringe is prepared in the same way with 120 µl of Peptide 1, volume in which 20 µl constitute the excess volume corresponding to the dead volume of the device.

Once the second syringe is filled with the dose of Peptide 1, it comes to replace the first empty syringe in the luer tip of the proximal connection (1a) of the hollow plunger (1). The cap that covers the needle is removed and the device is ready to inject.

Administration of an Insulin Solution at 100 IU/mL and a Peptide Solution at 200 μg/mL According to the Invention:

The injection is carried out according to the protocol described in Example 1.

Example 3 Demonstration of the Functioning of the Administrations Performed with a Device According to the Invention in a Third Configuration Solution of an analogue of Glucagon Like Peptide-1 (GLP-1) (Victoza®) at 6 mg/ml:

This solution is a commercial solution of Liraglutide marketed by NOVO NORDISK under the name of Victoza®. This product is an analogue of GLP-1. The solution is contained in a pre-filled, disposable Victoza® Pen Injector pen at a concentration of 6 mg/mL.

Before the first use, the Victoza® Injector pen is primed as described in the instruction manual to ensure that the device is not defective.

For this, a standard needle for an injector pen is used which is fixed on the device to check the flow and this is done with a standard needle for the injector pen.

The injector pen containing the Victoza® solution pen includes a window to view the dose of the selected product, with a special marking indicating the priming dose.

One turns the dose selector to this mark and by pressing the injection button one will make a drop of the product go out through the needle. If no product appears, repeat the procedure 3 times before changing the needle and repeat all the process detailed above with a new needle until a drop of product appears. This flow control operation is performed at each change of injector pen.

Slow Human Insulin Solution (Umuline® NPH) at 100 IU/mL:

This solution is a commercial solution of human insulin marketed by the company ELI LILLY under the name of Umuline® NPH. This product is an intermediate-acting insulin. The solution is contained in a commercial flask of 10 mL at a concentration of 100 IU/mL.

Preparation of the Device According to the Invention for a Solution of an Analogue of GLP-1 at 6 mg/ml and of an Insulin Solution at 100 IU/Ml from a Injector Pen and a Syringe In this configuration, the device according to the invention is equipped with a standard male luer stopper (not shown in FIG. 2, visible in (8) of FIG. 7) on the proximal connection (1a) and an injector pen adapter (11) which is clipped or screwed on the distal connection (2a) of the reservoir body (2) of the device. On this adapter (11) a injector pen containing the GLP-1 Victoza® analogue is screwed. It is possible and recommended to hold the needle device (4) facing upwards (hidden in the injector pen adapter (11)). By screwing the injector pen, the needle (4) of the distal connection (2a) acts as a injector pen connection and perforates the membrane of the cartridge.

A dose of 1.8 mg (300 μl) is selected on the injector pen. This dose is completely transferred into the reservoir through the needle (4).

While keeping the needle device (4) facing upwards, the injector pen is unscrewed while leaving the injector pen adapter (11) in place on the distal portion of the reservoir; in this way the needle (4) is protected.

The 520 μL syringe of Umuline® NPH insulin (volume in which 20 μl is the excess volume corresponding to the dead volume of the device) is prepared in a standard way from the commercial Umuline® NPH solution vial.

Administration of a Solution of a GLP-1 Analogue at 6 mg/ml and a Solution of Insulin at 100 UI/Ml According to the Invention:

The injection is carried out according to the protocol described in Example 1.

Example 4: Demonstration of the Operation of the Administrations Performed with a Device According to the Invention in a Fourth Configuration Glucagon Like Peptide-1 (GLP-1) Analogue Solution (Victoza®) at 6 mg/mL:

This solution is a commercial solution of Liraglutide marketed by NOVO NORDISK under the name of Victoza®. This product is an analogue of GLP-1. The solution is contained in a pre-filled, disposable Victoza® Pen Injector pen at a concentration of 6 mg/mL.

Prior to first use, the Victoza® Injector pen is primed as described in the Instructions for Use (Flow Verification) using a standard injector pen needle.

Slow Acting Insulin Analogue Solution (Lantus®) at 100 IU/mL:

This solution is a commercial solution of Glargine insulin marketed by SANOFI-AVENTIS under the name of Lantus®. This product is a slow insulin analogue. The solution is contained in a pre-filled and disposable SoloStar® injector pen at a concentration of 100 IU/mL.

Before each use, the SoloStar® injector pen containing the Lantus® solution is primed as described in the instructions for use to ensure that the device is not defective.

For this purpose, a standard needle for a injector pen is used which is fixed on the device to check the flow. The injector pen containing the Lantus® solution has a window allowing to see the dose of the selected product. One turns the dose selector to the mark 2 UI of insulin and pressing the injection button one makes a drop of product out through the needle. If no product appears, repeat the procedure 3 times before changing the needle and repeat all the process detailed above with a new needle until a drop of product appears. This flow control operation is performed before each use of the Lantus® Pen.

Preparation of the Device According to the Invention for a Solution of an Analogue of GLP-1 at 6 mg/ml and of an Insulin Solution at 100 IU/Ml from Two Injector Pens In this example, the device according to the invention is used as shown in FIG. 6. The injector pen adapter (11) is already in place on the distal connection (1a) of the reservoir (2) of the device. The injector pen containing the Victoza® solution is screwed onto the device held in the air (hidden by the injector pen adapter (11), that is to say the injector pen top and syringe connector device down). By screwing, the fixed needle (4) pierces the membrane of the cartridge containing the Victoza® solution.

A dose of 0.6 mg (i.e. 100 μL) is selected on the injector pen containing the Victoza® solution. This dose is completely transferred into the reservoir through the needle (4). While keeping the device with the needle (4) facing upwards, the injector pen is unscrewed while leaving the injector pen adapter (11) in place on the distal portion of the reservoir; in this way the needle (4) is protected.

The second injector pen containing the Lantus® insulin solution is screwed into the proximal connection (1a) of the hollow plunger (1). For a dose to be administered of 15 IU, a dose of 17 IU is selected on the injector pen to account for the dead volume of the device (2 IU).

Once the injector pen adapter (11) is removed to reveal the needle (4), the device is ready for injection.

Administration of a Solution of an Analogue of GLP-1 at 6 mg/ml and of an Insulin Solution at 100 IU/Ml Via the Device According to the Invention:

Once the administration needle is inserted at the injection site, the distal chamber is collapsed with the aid of the hollow plunger (1) to inject the Victoza® solution contained in the reservoir. This collapse is achieved by applying pressure to the device by holding the insulin injector pen by the body but without activating the injection button.

Then, by pressing the injection button of the Lantus® injector pen, insulin is injected and will occupy all the dead volumes inside the device after its passage, expelling the rest of the Victoza® solution. As for a regular injection with a injector pen, one waits 10 seconds with one's finger pressed on the injection button of the Lantus® injector pen to ensure that the entire dose has been dispensed.

Once the two products have been injected and the Lantus® injector pen unscrewed, the device is disposed of into a suitable container.

Example 5: Demonstration of the Operation of the Administrations Performed with a Device According to the Invention in a Fifth Configuration Solution of Triptorelin (Decapeptyl®) at 0.1 mg/ml:

This solution is a commercial solution of Triptorelin marketed by IPSEN under the name Decapeptyl®. This product is a GnRH analogue. The product is in the form of a lyophilisate to be reconstituted with a solvent ampoule.

Before each injection, the lyophilisate must be reconstituted with 1 mL of the solvent ampoule. Once the solution is completely clear and homogenized, it is ready for use.

Follitropin Beta Solution (Puregon®) at 300 IU/0.36 mL:

This solution is a commercial solution of follitropin beta marketed by MSD under the name Puregon®. This product is an analogue of the follicle stimulating hormone (FSH). The solution is contained in a 0.36 mL cartridge for use with the corresponding injector pen, the Puregon Pen®.

Before using it for the first time, the pen must be loaded with the Puregon® cartridge and primed as described in the instructions for use to ensure that the device is not defective.

For this, one uses a standard needle for the injector pen supplied with the Puregon® cartridge which is attached to the device to check the flow. The Puregon Pen® injector pen has a window for viewing the dose of the selected product. One turns the dose selector to the mark provided for this purpose and by pressing the injection button a drop of product is released through the needle. If no product appears, repeat the procedure 3 times before changing the needle and repeat all the process detailed above with a new needle until a drop of product appears. This flow control operation is performed only before the first use of the Puregon Pen®.

Preparation of the Device According to the Invention for a 300 UI/0.36 mL Solution of Follitropin Beta and a Solution of 0.1 mg/mL of Triptorelin from a Injector Pen and a Syringe In this configuration, the device according to the invention is equipped with a standard male luer stopper (not shown in FIG. 2, visible in (8) of FIG. 7) on the proximal connection (1a) and an injector pen adapter (11) which is clipped or screwed on the distal connection (2a) of the reservoir body (2) of the device. A Puregon Pen® pen is screwed on this adapter (11). It is possible and recommended to hold the needle device (4) facing upwards (hidden in the injector pen adapter (11)). By screwing the injector pen, the needle (4) of the distal connection (2a) acts as a injector pen connection and pierces the membrane of the cartridge.

A dose of 225 UI (270 µl) is selected on the injector pen. This dose is completely transferred into the reservoir through the needle (4).

While keeping the needle device (4) facing upwards, the injector pen is unscrewed while leaving the injector pen adapter (11) in place on the distal portion of the reservoir; in this way the needle (4) is protected.

The syringe containing 1020 µl of Decapeptyl® (volume in which 20 µl is the excess volume corresponding to the dead volume of the device) is prepared in a standard manner from the commercial vial of Decapeptyl® solution once reconstituted.

Administration of a Solution of Follitropin Beta at 300 IU/0.36 mL and a Solution of Triptoreline at 0.1 mg/mL According to the Invention:

The injection is carried out according to the protocol described in Example 1.

Example 6: Verification of the Non-Contamination of the Cartridge of the Injector Pen when Using the Device According to the Invention Glucagon Like Peptide-1 (GLP-1) Analogue Solution (Victoza®) at 6 mg/mL:

This solution is a commercial solution of Liraglutide marketed by NOVO NORDISK under the name of Victoza. The solution is contained in a pre-filled, disposable Victoza® Pen Injector Pen at a concentration of 6 mg/mL. Prior to first use, the Victoza® Injector pen is primed as described above in Example 2 (Flow Verification) using a standard injector pen needle.

Slow Insulin Analog Solution (Lantus®) at 100 IU/mL:

This solution is a commercial solution of insulin Glargine marketed by SANOFI-AVENTIS under the name of Lantus®. This product is a slow insulin analog. The solution is contained in a pre-filled, disposable SoloStar® Injector pen at a concentration of 100 UI/mL.

Assessment of Non-Contamination

In order to verify the action of the solid plunger (12) as a physical barrier preventing cross-contamination between the devices used to load the products, evidence of non-contamination is achieved with these injector pens. HPLC analysis determines whether the Lantus® injector pen has been contaminated, or contains traces of GLP1 (Victoza®) which was contained in the device according to the invention.

4 UI (40 µl) of the Lantus® injector pen cartridge used in Example 4 are discharged into a vial for HPLC analysis, supplemented to 1 mL with 0.1% acetic acid solution. In the same way a vial of Victoza® is prepared. After HPLC analysis, the two chromatograms are compared and the absence of a significant signal corresponding to GLP1 (Victoza®) on the chromatogram of the basal insulin solution (Lantus®) is verified.

The non-contamination of the cartridge contained in the Lantus® injector pen after use of the device according to the invention is demonstrated.

Example 7 Demonstration of the Operation and the Precision of Administrations Performed with a Device According to the Invention in a Fifth Configuration Preparation of the Device According to the Invention for 3 Distinct Solutions from Two Syringes and an Injector Pen To perform this example the device such as in Example 5 is used, with the difference that the proximal connection (1a) of the hollow plunger (1) is of the luer type.

Step 1: Filling the Distal Chamber (Fluid A)

This step is carried out as for the case of 2 fluids in Example 5.

Step 2: Filling the Second Chamber (Fluid B)

This step is carried out from a syringe previously filled with the dose of product B to be injected; as in Example 1, the syringe is connected by the proximal connection (1a) of the hollow plunger (1).

The dose of product B corresponding to the dose to be administered is then injected through the internal channel (1b) of the hollow plunger (1): the hollow plunger (1) being more mobile than the solid plunger (12), it moves relative to the reservoir, thus creating a second proximal chamber filled with fluid B. The dose of product B to be administered should not exceed a maximum volume (depending on the dimensions of the device).

Once the contents of the syringe B are completely discharged into the device, it is disconnected from the proximal connection (1a) to be replaced by the syringe C.

Step 3: Preparation of Syringe C (Fluid C)

The preparation of the syringe C corresponding to the third product to be discharged is carried out in a standard manner; however, taking into account the dead volumes of the device, a slight excess of product is added to the volume to be discharged. The excess of liquid depends on the dimensions of the device. Once the product syringe C is placed in the luer tip of the hollow plunger (1), the device is ready for injection.

Step 4: Injection

To perform the injection, it is necessary to maintain the plunger rod of the syringe C to prevent the product B contained in the second distal chamber formed between the solid plunger (12) and the hollow plunger (1) from going back into the syringe C. The product A is discharged by collapsing the solid plunger (12), then the product B by collapsing the hollow plunger (1), and finally the product C through the inner channel (1b).

Example 8 Demonstration of the Improvement of the Contact Surface at the Injection Point with a Device According to the Invention Versus a Standard Device This example was developed to measure the impact and pain of injections when the user pushes the needle through the skin, more particularly regarding the impact of the device with the skin at the end of penetration of the needle.

The elaborate model gives a visual representation of lesions created by this impact on the fragile surface, such as a thin sheet of paper for example.

The fragile surface is placed on the surface of a specific support to simulate the injections (injection pad in English) and is held in place and sufficiently tight to be able to practice the injection. This fragile surface will be marked or perforated during the injection depending on the support and the impact of the device in contact. The difference between the marks left by the tested devices makes it possible to check the convenience of their contact with the skin during a standard injection.

The pad equipped with the fragile surface is placed under a Lloyd machine (REF) to measure or program the force and speed of injection. The displacement at the same force and same speed is calculated over a distance from the beginning of penetration of the bevel of the cannula up to a pressure or deformation of 5.00 mm of the injection device in the injection simulator.

With a standard syringe equipped with a standard needle, the perforation is visible on a diameter of about 2 mm, accompanied by a deformation or visible tears on a diameter of about 1 cm on the fragile surface.

In the case of the device according to the invention equipped with the same needle, a central cutout corresponding to the cannula of the needle surrounded by the mark of the bearing circle of said device on the fragile surface. No tearing or sharp deformation is visible.

This model makes it possible to confirm that the use of a device according to the invention is less painful for the patient thanks to its extension allowing a better distribution of the injection forces on the surface of the skin.

In order to facilitate the understanding of the attached figures, the list given below summarizes the components of said figures:

LIST OF COMPONENTS

1. Hollow plunger
   a) Proximal connection
   b) Internal channel
2. Reservoir
   a. Distal connection
   b. Internal wall
   c. Bottom
3. Seal
4. Fixed needle
5. Syringe A
6. Standard female luer stopper
7. Syringe B
8. Standard male luer stopper
9. Bottle
10. Septum Flask
11. Injector pen adapter
12. Solid plunger
13. injector pen A
14. injector pen B
15. Standard needle
16. Safety valves
17. Channel
18. a. Surface variation of the inner wall
    b. Solid plunger surface variation
19. Depth control
20. Retaining notches
21. Security hooks

The invention claimed is:

1. A syringe-connector device for separately administering at least two products in controlled quantities by a single injection comprising:
   a reservoir having an inner wall; and
   a permanently open hollow plunger devoid of a closing-opening valve configured to be moved within the reservoir, said hollow plunger being open by an internal channel, from an end inserted inside said reservoir to another end in a proximal connection, said hollow plunger forming a sealed barrier with the inner wall of said reservoir, a stroke of the hollow plunger varying a volume of said reservoir according to a position of the hollow plunger from one end to another end in the interior of said reservoir, said proximal connection remaining constantly accessible outside of said reservoir, said reservoir being open at the one end thereof in a distal connection and at the other end thereof to introduce and allow said hollow plunger to circulate.

2. The device according to claim 1, further comprising at least one solid plunger movable within said reservoir, the at least one solid plunger being introduced into said reservoir before introduction of said hollow plunger,
   wherein said inner wall has, from the one end or the other end of said reservoir, a variation of a section of the inner wall configured to break the sealing between said solid plunger and said inner wall of said reservoir,
   said at least one solid plunger forming a sealed barrier with said inner wall of said reservoir with an exception of a distance on which the inner wall has a variation of its section, and
   the at least one solid plunger is configured such that when the at least one solid plunger is in contact with said one end or the other end of said reservoir, the at least one solid plunger is no longer sealed with said inner wall of said reservoir, which allows said products to pass between said at least one solid plunger and said inner wall of said reservoir.

3. The device according to claim 2, wherein the at least one solid plunger comprises a surface variation on a distal face thereof.

4. The device of claim 3, wherein the surface variation is of at least one groove or one slot.

5. The device of claim 2, wherein said inner wall has, from the one end or the other end of said reservoir, over a distance substantially equal to a thickness of said solid plunger, a variation of the section of the inner wall configured to break the sealing between said solid plunger and said inner wall of said reservoir, an increase in a diameter.

6. The device according to claim 1, wherein said device is configured to be connected to one or more of: one or more syringe-type administration devices, an injector pen, an injection bag, a bottle, a cartridge, an injector, a pump, a needle, a catheter, and a connector.

7. The device according to claim 1, wherein a diameter of said internal channel is of a size to allow passage of said at least two products to be administered.

8. The device of claim 7, wherein said diameter is greater in diameter than or at least equal to a diameter of a needle duct when the distal connection is provided with a needle.

9. The device according to claim 1, wherein said syringe-connector device comprises at a proximal end and/or a distal end connections which can be male or female, and be chosen from the connections of luer, luer-lock, screw, needle, septum, valve type.

10. The device according to claim 1, further comprising an adapter configured to allow fixing of an injector pen to said device, the adapter being fixed on said distal connection around a needle.

11. The device according to claim 1, wherein said syringe-connector device is configured to be sterilized before filling with materials compatible with the injection, wherein said reservoir is transparent, and
   wherein said hollow plunger or said reservoir is graduated.

12. The device according to claim 1, wherein a portion of the distal connection provided with a needle has a diameter comparable to that of said device, up to the cannula of the needle to provide support on skin at the time of injection.

13. The device according to claim 1, further comprising a lock that avoids reuse of the device, the lock being configured to control different injection depths of a needle when said hollow plunger is introduced to said one end or the other end of said reservoir.

14. A method for using the syringe-connector device as defined in claim 1, the method comprising:
   using the syringe-connector device by administrating the at least two products used in treatment of diabetes, infertility, hormone therapy, oncology as vaccines or in all treatments in which several close injections are to be performed.

15. The method according to claim 14, wherein several injections are performed using the syringe-connector device,
   wherein the at least two products are selected from at least one of the following groups a) to (c) are administered in the treatment of diabetes:
   a) insulin or an insulin derivative,
   b) GLP-1 or peptide analogues of GLP-1, and
   c) Glucagon or an analogue of Glucagon, in stable form in solution or in solid or freeze-dried form to be reconstituted.

16. The method of claim 15, wherein the insulin or the insulin derivative is selected from one or more of fast, semi-slow, slow, basal insulin, and insulin mixtures.

17. The method according to claim 14, wherein several injections are performed using the syringe-connector device,
   wherein the at least two products are selected from at least one of the following groups a) to c) are administered in the treatment of female infertility:
   a) the GnRH (gonadotropin-releasing hormone) agonists,
   b) the GnRH (Gonadotropin-releasing hormone) antagonists, and
   c) the follicle-stimulating hormone.

18. The method according to claim 14, wherein said at least two products to be administered in said volumes are in one or more of solid, semi-solid, lyophilized form, and non-lyophilized form and are preloaded or loaded when using said syringe-connector device.

19. A method for filling the syringe-connector device as defined in claim 1, the method comprising:
   closing one side of said reservoir with the hollow plunger; and
   filling the syringe-connector device by introducing the at least two products to be packaged inside said reservoir on a side of the distal connection or on a side of said hollow plunger before or after said hollow plunger is introduced into said reservoir.

20. The method according to claim 19, further comprising introducing the at least two products to be conditioned inside the reservoir that is partitioned in volumes thereof by a solid plunger and the hollow plunger on the side of the distal connection after said solid plunger is positioned in said reservoir or on the side of said hollow plunger, before or after said solid plunger or said hollow plunger is introduced into said reservoir.

* * * * *